(12) United States Patent
Avnir et al.

(10) Patent No.: US 9,643,168 B2
(45) Date of Patent: May 9, 2017

(54) METAL ENTRAPPED COMPOUNDS

(75) Inventors: David Avnir, Jerusalem (IL); Raed Abu-Reziq, Jatt Hamesholash (IL); Rachael Ben Knaz, Rehovot (IL); Itzik Yosef, Modiin (IL); Guy Nesher, Efrat (IL); Gad Marom, Jerusalem (IL)

(73) Assignee: Yissum Research Development Company of the Hebrew University of Jerusalem, Ltd., Jerusalem (IL)

( * ) Notice: Subject to any disclaimer, the term of this patent is extended or adjusted under 35 U.S.C. 154(b) by 0 days.

(21) Appl. No.: 12/783,916

(22) Filed: May 20, 2010

(65) Prior Publication Data

US 2010/0297724 A1    Nov. 25, 2010

Related U.S. Application Data

(60) Provisional application No. 61/180,152, filed on May 21, 2009.

(51) Int. Cl.
| | | |
|---|---|---|
| *C12N 11/14* | (2006.01) | |
| *B01J 31/00* | (2006.01) | |
| *B01J 23/50* | (2006.01) | |
| *B01J 31/06* | (2006.01) | |
| *B01J 31/22* | (2006.01) | |

(Continued)

(52) U.S. Cl.
CPC .......... *B01J 31/003* (2013.01); *B01J 23/50* (2013.01); *B01J 31/06* (2013.01); *B01J 31/2269* (2013.01); *B01J 31/2273* (2013.01); *B01J 31/2278* (2013.01); *B01J 31/2295* (2013.01); *B01J 31/2404* (2013.01); *B01J 31/2409* (2013.01); *C07C 5/03* (2013.01); *C12N 11/14* (2013.01); *B01J 2231/645* (2013.01); *B01J 2531/0252* (2013.01); *B01J 2531/0263* (2013.01); *B01J 2531/0266* (2013.01); *B01J 2531/822* (2013.01); *B01J 2531/824* (2013.01); *B01J 2531/827* (2013.01)

(58) Field of Classification Search
CPC . B01J 23/50; B01J 31/003; B01J 31/06; B01J 31/2269; B01J 31/2273; B01J 31/2278; B01J 31/2295; B01J 31/2404; B01J 31/2409; C12N 11/14; C07C 5/03
USPC .......................................................... 75/252
See application file for complete search history.

(56) References Cited

U.S. PATENT DOCUMENTS 5,008,158 A * 4/1991 Fang ..................... C22C 49/00
                                                    164/97
5,100,736 A * 3/1992 London ............... C22C 32/0094
                                                    419/10

(Continued)

OTHER PUBLICATIONS

A Hovestad, et al., "Electrochemical deposition of zinc-polystyrene composites in the presence of surfactants," Journal of Applied Electrochemistry 29 (1999) 331-338.*

(Continued)

*Primary Examiner* — Jessee Roe
*Assistant Examiner* — Christopher Kessler
(74) *Attorney, Agent, or Firm* — Vorys, Sater, Seymour and Pease LLP

(57) ABSTRACT

The present invention provides a composite comprising at least one hydrophobic organic compound and a matrix of at least one metal; wherein said at least one hydrophobic compound is entrapped within said matrix, compositions comprising at least one composite and methods of its preparation.

11 Claims, 21 Drawing Sheets

(51) Int. Cl.
  B01J 31/24        (2006.01)
  C07C 5/03         (2006.01)

(56) References Cited

U.S. PATENT DOCUMENTS

2009/0061226 A1* 3/2009 Banin et al. .................. 428/402
2009/0136707 A1* 5/2009 Ueno ............................ 428/113

OTHER PUBLICATIONS

Nesher et al., "Polyaniline Entrapped in Silver: Structural Properties and Electrical Conductivity" Advanced Functional Materials vol. 19, Issue 8, pp. 1293-1298, Apr. 23, 2009.*

Yosef, et al., "Metal-Organic Composites: The Heterogeneous Organic Doping of the Coin Metals-Copper, Silver, and Gold", Chem. Mater., vol. 18, pp. 5890-5896, (2006).

Behar-Levy, et al., "Entrapment of Organic Molecules within Metals: Dyes in Silver", Chem. Mater., vol. 14, pp. 1736-1741, (2002).

Behar-Levy, et al., "Entrapment of Organic Molecules within Metals. 2. Polymers in Silver", Chem. Mater., vol. 16, pp. 3197-3202, (2004).

Behar-Levy, et al., "Silver Doped with Acidic/Basic Polymers: Novel, Reactive Metallic Composites", Adv. Funct. Mater., vol. 15, pp. 1141-1146, (2005).

Shier, et al., "Organically Doped Metals—A New Approach to Metal Catalysis: Enhanced Ag-Catalyzed Oxidation of Methanol", Adv. Funct. Mater., vol. 17, pp. 913-918, (2007).

Behar-Levy, et al., "Chirality Induction in Bulk Gold and Silver", Adv. Mater., vol. 19, pp. 1207-1211, (2007).

Nesher, et al., "Metal-Polymer Composites: Synthesis and Characterization of Polyaniline and Other Polymer@Silver Compositions", Chem. Mater., vol. 20, pp. 4425-4432, (2008).

Gertner, et al., "Drug Delivery from Electrochemically Deposited Thin Metal Films", Electrochemical and Solid-State Letters, vol. 6, No. 4, pp. J4-J6, (2003).

Neouze, et al., "Entrapment of an Ionic Liquid in a Metallic Silver Matrix through Precipitation", Aust. J. Chem., vol. 61, pp. 329-331, (2008).

Yosef, et al., "Entrapment of an Organometallic Complex within a Metal: A Concept for Heterogeneous Catalysis", J. Am. Chem. Soc., vol. 130, pp. 11880-11882, (2008).

Ben-Knaz, et al., "Bioactive enzyme-metal composites: The entrapment of acid phosphatase within gold and silver", Biomaterials, vol. 30, pp. 1263-1267, (2009).

* cited by examiner a b

METAL ENTRAPPED COMPOUNDS

This application claims the benefit of prior U.S. provisional patent application No. 61/180,152 filed May 21, 2009, the contents of which are hereby incorporated by reference in their entirety.

This invention was made with US government support under FA9550-06-1-0227 awarded by AFOSR. The government has certain rights in the invention.

FIELD OF THE INVENTION

This invention relates to composites comprising at least one metal entrapping at least one organic compound, methods of their preparation, and methods of using them.

RELATED ART

The following publications are considered pertinent for describing the state of the art in the field of the invention:
1. Yosef, I.; Avnir, D. *Chem. Mater.* 2006, 18, 5890-5896.
2. Behar-Levy, H.; Avnir, D. *Chem. Mater.* 2002, 14, 1736-1741.
3. Behar-Levy, H.; Shter, G. E.; Grader, G. S.; Avnir, D. *Chem. Mater.* 2004, 16, 3197.
4. Behar-Levy, H.; Avnir, D. *Adv. Funct. Mater.* 2005, 15, 1141.
5. Shter, G. E.; Behar-Levy, H.; Gelman, V.; Grader, G. S.; Avnir, D. *Adv. Funct. Mater.* 2007, 17, 913-918.
6. Behar-Levy, H.; Neumann, O.; Naaman, R.; Avnir, D. *Adv. Mater.* 2007, 19, 1207.
7. Nesher, G.; Marom, G.; Avnir, D. *Chem. Mater.* 2008, 20, 4425-4432.
8. (a) Entrapment during electrochemical thin film deposition has been reported in: Gertner, M. E.; Schlesinger, M. *Electrochem. Solid-State Lett.* 2003, 6, J4. (b) For entrapment of Ionic liquids in silver: Neouze, M. A.; Litschauer, M; *Australian Journal of Chemistry* 2008, 61(5) 329-331.
9. Yosef, I.; Abu-Reziq, R.; Avnir, D *J. Am. Chem. Soc.* 2008 130, 11880-11882.
10. Ben-Knaz, R.; Avnir, D. *Biomaterials* 30 (2009) 1263-1267.

All publications mentioned in this specification are herein incorporated in their entirety by reference into the specification, to the same extent as if each individual publication, patent or patent application was specifically and individually indicated to be incorporated herein by reference.

SUMMARY OF THE INVENTION

In the first aspect, the invention provides a composite comprising at least one hydrophobic organic compound and a matrix of at least one metal; wherein said at least one hydrophobic compound is entrapped within said matrix.

When referring to a composite or composite material it should be understood to encompass a multi-component material, comprising multiple, different phase domains, in which at least one type of phase domain is a continuous phase.

When referring to a matrix formed by said at least one metal, it should be understood to encompass a three dimensional continuous aggregate of metallic crystallites and/or particles (in some embodiments particles have at least one dimension having a length of between about 5 nm to about 100 nm) connected via physical and/or chemical bonds such as for example electrostatic and/or Van-der-Waals forces, thereby forming pores and inner voids in said three dimensional aggregate capable of entrapping molecule(s) therein. In some embodiments, an organic species is said to be entrapped in metal if the organic species is surrounded by metallic particles and immobilized to the metal by forces other than covalent bonding, for example, steric entrapment, van der Waals forces, hydrogen bonding, and/or ionic bonding.

In some embodiments, said metal matrix entrapping said agent(s) has pore size (and/or inner voids formed by three dimensional matrix structure) of between about 0.1 to about 30 nm.

In some embodiments, the entrapped species is not readily washed away.

Alternatively or additionally, the organic species forms a nanometric scale hybrid with the metal, as may be verified, for example, by microscopy, and/or by pore size distribution analysis of the composite material before and after extraction of the organic species from the metal.

In some embodiments, the metal entrapping the organic material retains its appearance, for example, its metallic luster, and in gold and copper, their typical color.

Composites comprising organic materials entrapped in metals according to embodiments of the present invention occur in one or more of the following particle shape and/or size: granules, powders, sub-micron particles, or thin films. The thin films are optionally of a thickness of between about 0.5 nm (a monolayer) and about 200 nm. In some embodiments, the particles are compressed, optionally under heat, like in sintering, to provide disks in various sizes, ranging up to several cm in diameter. In some embodiments, said at least one hydrophobic organic compound is selected from at least one hydrophobic oligomer, at least one hydrophobic polymer, at least one hydrophobic enzyme, at least one hydrophobic organometallic complex, or any mixtures thereof.

When referring to a hydrophobic compound or a hydrophobic organic compound entrapped within said metal matrix, it should be understood to encompass any organic compound having low to substantially negligible solubility in water or polar solvents (having similar polarity).

In some other embodiments said at least one hydrophobic organic compound is selected from at least one hydrophobic oligomer, at least one hydrophobic polymer. In other embodiments said at least one hydrophobic organic compound is at least one hydrophobic enzyme. In further embodiments said at least one hydrophobic organic compound is at least one hydrophobic organometallic complex.

In some embodiments, the hydrophobic compound is a polymer having hydrophilic and hydrophobic groups, and the number ratio between them is between 1:10 and 1:100. Optionally, the ratio is larger than 1:100. Optionally, the hydrophobic compound is a polymer, composed only of hydrophobic monomers. A hydrophobic monomer is optionally defined as a monomer having water solubility of below 1 g per liter.

To date, only water soluble moieties could be entrapped, because all the available entrapping methods involved reduction of a metallic ion in an aqueous solution that contained both ions of the entrapping metal and dissolved entrapped moiety. Some embodiments provide a new entrapment methodology, specifically (but not solely) useful for entrapping water insoluble compounds.

In an exemplary embodiment N,N-dimethylformamide (DMF) is used as the solvent. DMF was found to be both an excellent solvent for many hydrophobic polymers and a potent reducing agent for some metal cations. It was found that its activity as a reducing agent can be triggered at will by adding water to the solution. Optionally, the molar ratio between the added water and the metal ion in the solution is small enough not to affect the dissolution properties of DMF. In some embodiments, this ratio is between 1:100 and 1:10000 (water:DMF).

In some further embodiments, said entrapped at least one hydrophobic compound is substantially retained within said matrix.

The term "retained within at least one metal matrix" should be understood to mean the ability of said at least one metal matrix to maintain the hydrophobic compound with substantially minimal leakage to the surrounding environment, i.e. a surrounding solvent.

In some embodiments, for example when the entrapped at least one compound is at least one polymer or oligomer, such a solvent is at least one hydrophobic solvent. In other embodiments, said solvent is at least one hydrophilic solvent.

When relating to said at least one hydrophobic compound being entrapped within said matrix, it should be understood to encompass the enclosure of at least one type of compound in the inner voids and/or pores formed in said metallic matrix. The compounds are held enclosed within the metallic matrix via multiple physical and chemical adsorptive interactions such as covalent, electrostatic and Van-der-Waals, $\pi$-$\pi$ and/or $\sigma$-$\pi$ interactions, charge-transfer interactions and hydrophobic interactions.

In some embodiments, the entrapped compound does not dissolve in water. In some other embodiments, the entrapped moiety is so hydrophobic that it does not dissolve in a hydrophilic solvent (such as for example water) even if such a solvent further comprises surface active agents, which generally increase the solubility of hydrophobic compounds. For example, some organic species are entrapped in metals according to embodiments of the present invention, and not dissolved in water even if they are present in a concentration lower than the CMC (critical micelle concentration) of the surfactant.

In some embodiments, the solubility of hydrophobic compound in water at 20° C. is lower than 0.1 g per liter, optionally lower than 0.01 g per liter. In some embodiments, said at least one hydrophobic oligomer or polymer have a molecular weight of at least about 10 kdalton.

In some embodiments, said at least one hydrophobic enzyme is selected from any type of a hydrolase enzyme, an esterase enzyme and a peptidase enzyme and any mixture thereof.

Hydrolase enzymes can be classified as EC 3 enzymes. Hydrolases can be further classified into several subclasses, based upon the bonds they act upon: EC 3.1: ester bonds (esterases: nucleases, phosphodiesterases, lipase, phosphatase), EC 3.2: sugars (DNA glycosylases, glycoside hydrolase), EC 3.3: ether bonds, EC 3.4: peptide bonds (Proteases/peptidases), EC 3.5: carbon-nitrogen bonds, other than peptide bonds, EC 3.6 acid anhydrides (acid anhydride hydrolases, including helicases and GTPase), EC 3.7 carbon-carbon bonds, EC 3.8 halide bonds, EC 3.9: phosphorus-nitrogen bonds, EC 3.10: sulfur-nitrogen bonds, EC 3.11: carbon-phosphorus bonds, EC 3.12: sulfur-sulfur bonds, EC 3.13: carbon-sulfur bonds.

An esterase is a hydrolase enzyme that splits esters into an acid and an alcohol in a chemical reaction with water called hydrolysis. A wide range of different esterases exist that differ in their substrate specificity, their protein structure, and their biological function. Acetylesterase (EC 3.1.1.6): Cholinesterase, Acetylcholinesterase, Pseudocholinesterase, Pectinesterase (EC 3.1.1.11), EC 3.1.2: Thiolester hydrolases: Thioesterase, Ubiquitin carboxy-terminal hydrolase L1, EC 3.1.3: Phosphoric monoester hydrolases: Phosphatase (EC 3.1.3.x), Alkaline phosphatase, Phosphodiesterase (PDE), cGMP specific phosphodiesterase type 5, Fructose bisphosphatase (3.1.3.11), EC 3.1.4: Phosphoric diester hydrolases, EC 3.1.5: Triphosphoric monoester hydrolases, EC 3.1.6: Sulfuric ester hydrolases (sulfatases), EC 3.1.7: Diphosphoric monoester hydrolases, EC 3.1.8: Phosphoric triester hydrolases, Exonucleases (deoxyribonucleases and ribonucleases): EC 3.1.11: Exodeoxyribonucleases producing 5'-phosphomonoesters EC 3.1.13: Exoribonucleases producing 5'-phosphomonoesters EC 3.1.14: Exoribonucleases producing 3'-phosphomonoesters EC 3.1.15: Exonucleases active with either ribo- or deoxy-, Endonucleases (deoxyribonucleases and ribonucleases): Endodeoxyribonuclease, Endoribonuclease either deoxy- or ribo-.

A protease (also termed peptidase or proteinase) is an enzyme that conducts proteolysis, i.e., begins protein catabolism by hydrolysis of the peptide bonds that link amino acids together in the polypeptide chain forming the protein. Proteases are functional in acidic conditions except for the alkaline proteases family. Proteases are can be classified into six broad groups: Serine proteases, Threonine proteases, Cysteine proteases, Aspartate proteases, Metalloproteases, Glutamic acid proteases. Alternatively, proteases may be classified by the optimal pH in which they are active: Acid proteases, Neutral proteases, Basic proteases (or alkaline proteases).

In further embodiments, said at least one hydrophobic organometallic complex is any transition family element organic complex.

Such transition family elements include any element whose atom has an incomplete d sub-shell, or which can give rise to cations with an incomplete d sub-shell.

In another embodiment of the invention, said at least one metal is selected from Au, Ag, Cu, Zn, Pt, Pd, Ti and Co, and any mixtures thereof. Such elements include d-block atoms having between 1 and 10 d electrons. Non limiting lists of organic complexes of such elements are given herein below. In some embodiments, such organometallic complexes are catalysts, wherein their catalyzing properties are either similar or enhanced by the entrapment within said metal matrix.

It should be understood that when referring to two or more metals comprised in the composite of the invention, said metal matrix may be composed of a mixture of at least two metals or a metallic alloy, such as for example alloys of Ag and Zn, alloys of Ag and Au, alloys of Ag and Cu, alloys of Cu and Zn and so forth. An alloy according to the invention is a partial or complete blend of one or more elements in a metallic matrix. A complete solid solution alloys displays single solid phase microstructure, while a partial solution may have two or more phases that may be homogeneous and/or heterogeneous in distribution.

In yet a further embodiment of the invention, said entrapped at least one hydrophobic compound and at least one metal have a ratio of between about 0.05 to about 20 weight %.

In another embodiment, said at least one metal matrix has pore size of between about 0.1 to about 30 nm.

Optionally, the obtained composition is mesoporous, that is, with average pore sized in the range of 1-100 nm. In some embodiments, 0.1-40%, optionally 0.1-25% of the hybrid material is composed of hydrophobic moiety.

In a further embodiment, a composite of the invention has a surface area of between 0.1 and 20 m$^2$ per gram, as determined by N$_2$-BET.

In another one of its aspects the invention provides a composition comprising at least one composite of the invention.

In a further aspect the invention provides a heterogeneous catalyst comprising at least one composite comprising at least one hydrophobic organometallic complex and a matrix of at least one metal; wherein said at least one hydrophobic organometallic complex is entrapped within said matrix.

In yet another aspect, the invention provides a heterogeneous catalyst comprising at least one composite comprising at least one hydrophobic enzyme and a matrix of at least one metal; wherein said at least one hydrophobic enzyme is entrapped within said matrix.

The invention further encompasses a method comprising:
(a) providing a mixture comprising at least one solvent, at least one metal salt,
and at least one hydrophobic compound or a precursor thereof;
(b) reducing said metal salt, so as to obtain a matrix of said at least one metal entrapping said at least one hydrophobic compound.

An aspect of the invention concerns a method of entrapping a hydrophobic moiety in metal. In an exemplary embodiment the method comprises providing a solution comprising: a solvent, a salt of the metal, and the hydrophobic moiety; and reducing the metal of the metal salt in the presence of dissolved hydrophobic moiety, so as to obtain the hydrophobic moiety entrapped in the metal. This method is particularly useful when the solvent is suitable for the metal. Solvents of particular suitability to copper, silver, and gold include, but are not limited to hexane, tuloene, amphiphilic solvents, for example, DMF, and DMSO, and mixtures of two or more thereof.

Optionally, reducing the metal of the metal salt in an amphiphilic solvent comprises adding to the solution water, optionally, in a ratio of between 1:10 and 1:1 (metal-ion: water) to the metal ions in the solution.

Thus, an embodiment of the invention concerns a method of preparing a composite comprising a metal cation entrapped in metal. The cation is optionally complexed with one or more organic ligands. The method comprises reducing a cation of the entrapping metal in the presence of a cation of the entrapped metal. In some embodiments, the reduction reaction takes place in the presence of at least one aqueous solvent, for example, water.

To reduce the ion of the entrapping metal with only minimal reduction of the entrapped metal ion, the reduction is optionally carried out in considerable excess of entrapping metal. Examples of considerable excess are a ratio of between 1:50 and 1:1000 between entrapped and entrapping metal ions.

In some other embodiments, the reducing agent is chosen so as not to react with the organic species to be entrapped, but still be powerful enough for reducing the metal. In other embodiments, the reducing agent is heterogeneous to the reaction solution. In an exemplary embodiment, the entrapping metal is silver, the entrapped complexed metal is rhodium, and the reducing agent is zinc powder. Optionally, the ratio between the reducing agent and the metal salt is stoichiometric.

In one exemplary embodiment, there is provided a method of preparing a heterogeneous catalyst comprising an organometallic complex. The method comprises providing a homogeneous catalyst comprising the organometallic complex, and entrapping the organometallic complex in metal. Optionally, entrapping the complex in metal comprises reducing a cation of the metal in the presence of the organometallic complex. In some embodiments, the reduction process is stopped after at least 50% of the complex is entrapped. Optionally, the reducing is under such conditions that leave most of the entrapped organometallic complex not reduced. Optionally, only a small portion of 10% or less of the entrapped complex is reduced. Optionally, the small portion is of 1% or less of the entrapped complex.

In another aspect, there is provided an enzymatically active composite comprising an enzymatically active enzyme entrapped in metal. Preferably, the entrapped enzyme is active to catalyze the same reactions catalyzed by the free enzyme. Optionally, the entrapped enzyme is active under different conditions than the free enzyme. In some embodiments, the entrapped enzyme is active under a broader range of conditions than the free enzyme. For example, in some embodiments, the entrapped enzyme is active at pH values, where the free enzyme is practically inactive.

In some embodiments, for example, under extreme pH conditions, the entrapped enzyme is more active than the free enzyme under the same conditions.

In some embodiments, the metal entrapping the enzyme is by itself catalytic, catalyzing a process that is the same as or different from the process catalyzed by the enzyme.

In another one of its aspects the invention provides a biosensor comprising at least one composite comprising at least one hydrophobic enzyme and a matrix of at least one metal; wherein said at least one hydrophobic enzyme is entrapped within said matrix.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any integer or step or group of integers and steps.

In order to understand the invention and to see how it may be carried out in practice, embodiments will now be described, by way of non-limiting example only, with reference to the accompanying drawings, in which:

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 22 represents a schematic diagram of a biosensor, shown as Scheme 7, which are components of a biosensor utilizing a composite of the invention.

DETAILED DESCRIPTION OF EMBODIMENTS

Figures 1A, 1B, 1C, 1D:
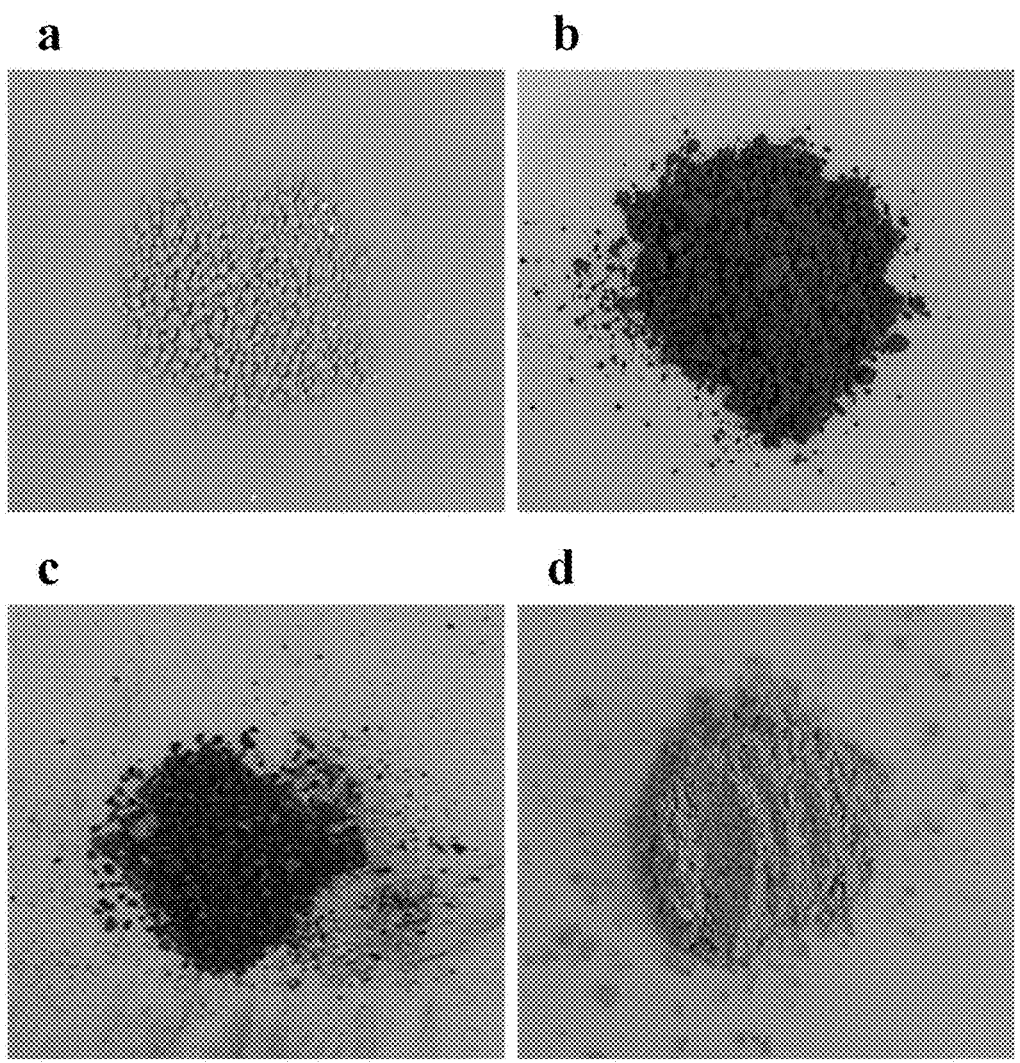
FIGS. 1a-1d are macroscopic view of composites of the invention: (a) Ag, (b) PANI@Ag, (c) PAN@Ag, (d) PS@Ag.

In order to understand the invention and to see how it may be carried out in practice, embodiments will now be described, by way of non-limiting example only, with reference to the accompanying drawings.

Entrappment of Hydrophobic Polymers

Materials:

Polyaniline (PANI, emeraldine base, MW~100,000) and $AgNO_3$ were from Aldrich. Polyacrylonitrile (PAN, MW~150,000) and monocarboxy-terminated-polystyrene (PS, MW~150,000) were from Scientific Polymer Products, NY. Silver nanoparticles (<100 nm, 99.5%) were from Sigma.

Entrapment Procedure of PANI:

To a hot stirred solution of 50 ml DMF, 0.1 g (0.0009 moles of monomers) of PANI was added and after 1 min 1.70 g $AgNO_3$ (0.01 moles) was added as well. The combined solution was heated to 100° C. to accelerate dissolution and stirred for 2 hrs, after which 5.0 ml (0.25 moles) of distilled water was added. The reduction, which begins immediately with the addition of the water and is clearly apparent, was carried out over-night forming PANI@Ag. The precipitate was filtered and washed with two portions of 10 ml DMF and one portion of 10 ml water and dried under vacuum for a few hours. The resulting material, 1.0 g of PANI@Ag, contained ~95% of the initial polymer used in the reaction mixture, as determined by TGA analysis. The yield with respect to the $AgNO_3$ is ~90% and the color of the silver was changed by the presence of the polymer into gray-black.

Entrapment Procedure of PAN:

To a hot and stirred solution solution of 50 ml DMF, 0.1 g of PAN (0.0015 moles of monomers) was added and after 15 min 1.70 g $AgNO_3$ (0.01 moles) was added as well. A reaction between the PAN and the silver ions begins immediately and the solution turns black after a day. The combined solution was stirred for another 3 days after which 5.0 ml (0.25 moles) of distilled water was added. Precipitation of PAN@Ag (black material, FIG. 1c) begins after the addition of water, and the reduction/entrapment reaction was continued over-night. The precipitated PAN@Ag was filtered and washed with 2 portions of 10 ml DMF and one portion of 10 ml water and dried under vacuum for a few hours. The resulting material, 0.8 g, contained ~79% of the initial polymer used in the reaction mixture, as determined by TGA analysis. The yield with respect to the $AgNO_3$ is ~85%.

Entrapment Procedure of PS:

To 20 ml toluene, 0.1 g of monocarboxy-terminated-PS (0.001 moles of monomers) was added under stirring. After 15 min, a solution of 1.70 g $AgNO_3$ (0.01 moles) in 30 ml of DMF was added. After the mixing the stirred solution remains clear. The flask was covered (to limit photoreduction of the silver ions before the addition of the water and stirred overnight (to enhance interaction between the PS molecules and the silver ions, probably through the carboxy group. The next day the solution was heated up to 80° C. for 2 hrs and than 1.0 ml of (0.05 moles) distilled water was added gently to the solution. Great care should be taken not to have phase separation during the addition of water. Precipitation of PS@Ag (gray material) begins after the addition of the water, and the reduction/entrapment reaction was continued over-night. The precipitated PS@Ag was filtered and washed with one portion of 10 ml toluene and one portion of 10 ml DMF and dried under vacuum for a few hours. The resulting material, 0.6 g, contained ~35% of the initial polymer used in the reaction mixture, as determined by TGA analysis. The yield with respect to the $AgNO_3$ is ~70%.

Adsorption Vs. Entrapment Measurements:

To check if the PANI was entrapped in the silver or just adsorbed thereon, the following experiments were carried out. The pure metal was prepared as described above, but without the presence of the organic material. 1 g of the obtained metal was stirred with 0.1 g of PANI at room temperature for 24 hours. The solution was filtered, and its UV-VIS spectrum was analyzed to find the concentration of PANI in the solution. Similarly, 1 g of commercially available metal nanoparticles (100 nm in diameter) was stirred with 0.1 g PANI. The solution was filtered, and the amount of PANI was determined based on the UV-VIS spectrum of the filtered solution.

Extraction Measurements:

Another test was run to ensure that the hydrophobic polymers were indeed entrapped in the metal. 0.1 g of the product was stirred with 15.0 ml of solvent over-night. In case of PAN and PANI, the test was run twice, once with DMF and once with DMSO, and in case of PS, the test was run only with toluene.

Instrumentation:

UV-Vis absorption spectroscopy was carried out with a Hewlett-Packard 8452A diode-array Uv-Vis spectrophotometer. XRD measurement were carried out with Philips automated powder diffractometer (with PW1830 generator, PW1710 control unit, PW1820 vertical goniometer, 40 KV, 35 mA, Cu Kα (1.5405 Å)). SEM was carried on a Sirion (FEI) HR-SEM instrument (operating voltage is indicated for each picture). Thermogravimetric thermal analysis (TGA) was preformed on a Mettler TC10A/TC15 TA controller from 25 to 600° C. at a heating rate of 10° C./min in flowing dry air. For a more exact analysis of the TGA graphs, the derivative weight loss was calculated using the supplied software. Surface area and porosity were determined from nitrogen adsorption/desorption isotherms with a Micromeritics ASAP-2020 physisorption instrument, using the Brunauer-Emmett-Teller (BET) equation to characterize the overall surface area and Barret-Joyner-Hallender (BJH) equation to determine the surface area in the mesoporous region. Density was determined from weight/volume analysis using Micromeritics AccuPyc 1340 gas pycnometer instrument using helium as a displacing gas. The XPS (X-ray Photoelectron Spectroscopy) measurements were performed on a Kratos Axis Ultra X-ray photoelectron spectrometer. Spectra were acquired with monochromated Al Kα (1486.7 eV) X-ray source with 0° takeoff angle. The pressure in the test chamber was maintained at $1.5 \times 10^{-9}$ Torr during the acquisition process. High resolution XPS scans were collected for N 1s, C 1s, O 1s and Ag 3d peaks with pass energy 20 eV with the step size of 0.1 eV. Data analysis and processing were performed with Vision processing data reduction software (Kratos Analytical Ltd.) and CasaXPS (Casa Software Ltd.).

Figures 2A, 2B, 2C, 2D:
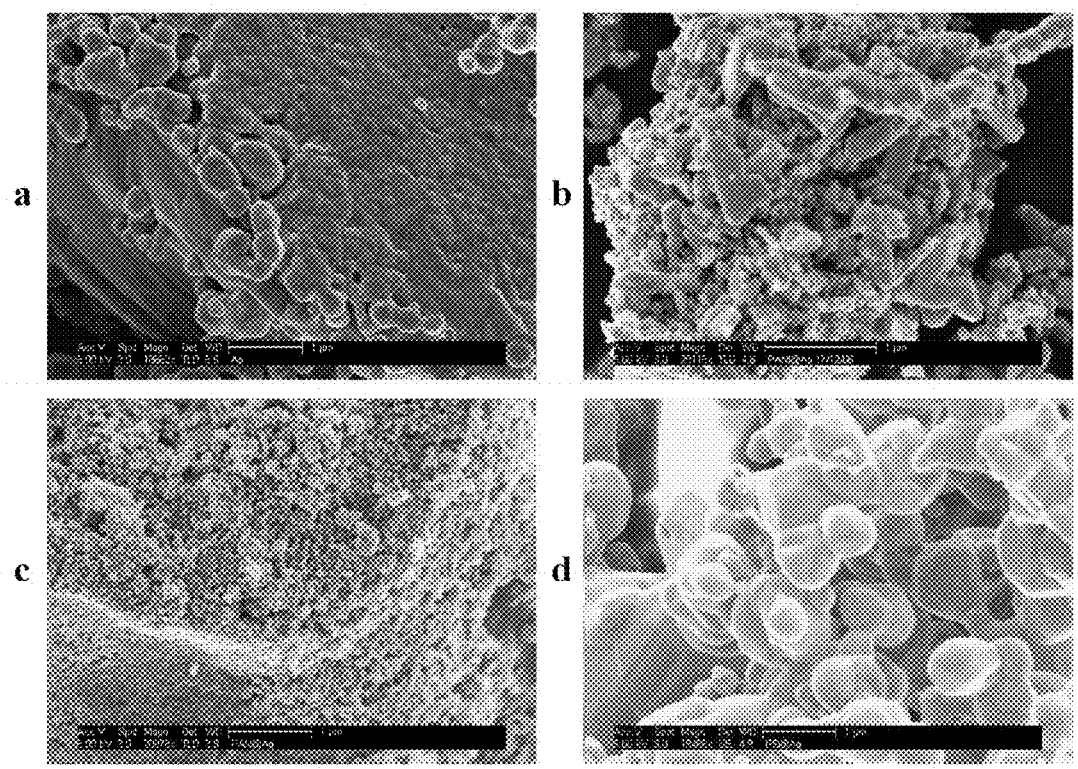
FIGS. 2a-2d are high resolution SEM images of composites of the invention (a) Ag, (b) PANI@Ag, (c) PAN@Ag, (d) PS@Ag.

Characterization of PANI@Ag Composites:

FIGS. 1a and 1b show that the introduction of the hydrophobic polymer has changed the outer appearance of silver aggregates. While the metal prepared by reducing the metal salt in the absence of PANI, as described above, takes the classical form of a silvery gray and dense spherical granules (FIG. 1a), PANI@Ag composite is a grayish black powder (FIG. 1b). The SEM photos (FIG. 2) confirm these observations, showing the dense and non-porous pure silver metal (FIG. 2a) as compared with the nano-size particles (100-300 nm) of PANI@Ag composites (FIG. 2b). The density of the pure silver spheres (Table 1, below) is high (10.4 g/ml), and close to the density of crystalline bulk Ag. The composite exhibits significantly lower density (~7.2 g/ml), reflecting both the contribution of the organic component and the interstitial porosity between the nanocrystals that form the bulk material.

TABLE 1

Typical densities of the metal-polymer composites

| Sample | Density (g/ml) |
| --- | --- |
| PANI@Ag | 7.2 |
| PAN@Ag | 6.6 |
| PS@Ag | 8.6 |
| Ag | 10.4 |
| Bulk - Ag[a] | 10.5 |

[a]CRC Handbook of Chemistry and Physics 81st ed.

$N_2$ adsorption-desorption BET experiments (Table 2 and FIG. 3) provide additional supportive data which confirm the visual observations and density measurements. A significant surface area ($N_2$-BET) increase from pure Ag to the composite can be seen in Table 2, indicating higher porosity—or in fact, mesoporosity—as is indicated by the high location of the P/P° hysteresis loops in FIG. 3a). It is noted though that this mesoporosity is considered low compared to those of classical adsorbents in the hundreds of $m^2/g$ range, such as silica materials. Moreover, the excellent fit of the experimental values and the BET equation (FIG. 3c) reflects a high level of adsorption site homogeneity, which in turn, points at a high uniformity of the composite material.

TABLE 2

Typical surface area and pore size values

| Sample | BET - Surface area ($m^2/g$) | BJH - Pore Volume (ml/g) | BJH - Pore size (nm) |
| --- | --- | --- | --- |
| PANI@Ag | 4.4 | 0.03 | 19 |
| PAN@Ag | 8.6 | 0.04 | 21 |
| PS@Ag | 0.05 | 0.0002 | 135 |
| Ag | 0.003 | — | — |

XRD analysis (Table 3) shows clearly that the metallic component of PANI@Ag comprises crystalline FCC Ag, similarly to sliver that does not entrap PANI. The characteristic diffraction lines of the metal remain unchanged, while no peaks of silver salts or silver oxide can be seen. Application of the Scherrer equation with the width of the diffraction peak at half height indicates that the elementary building block of the aggregated silver nanocrystals, is in the ~40 nm size range, compared with ~60 nm of pure silver. Without being bound by theory it is speculated that the size reduction is caused by the polymer restricting the growth of the granule.

TABLE 3

X-ray diffraction patterns and crystallite size

| | Lit. data Ag[a] | | Ag bulk | | PANI@Ag | | PAN@Ag | |
| --- | --- | --- | --- | --- | --- | --- | --- | --- |
| Plane (hkl) | Int | d(Å) | Int | d(Å) | Int | d(Å) | Int | d(Å) |
| 111 | 100 | 2.359 | 1870 | 2.36 | 2080 | 2.36 | 720 | 2.36 |
| 200 | 40 | 2.044 | 840 | 2.04 | 625 | 2.04 | 222 | 2.04 |
| 220 | 25 | 1.445 | 430 | 1.44 | 450 | 1.44 | 188 | 1.44 |
| Crystallite Size[b] (nm) | — | | 59.7 | | 43.3 | | 27.8 | |

[a]2003 JCPDS - International Center for Diffraction Data
[b]Calculated from the XRD patterns using Scherrer's equation.

Figures 4A, 4B, 4C, 4D, 4E, 4F:
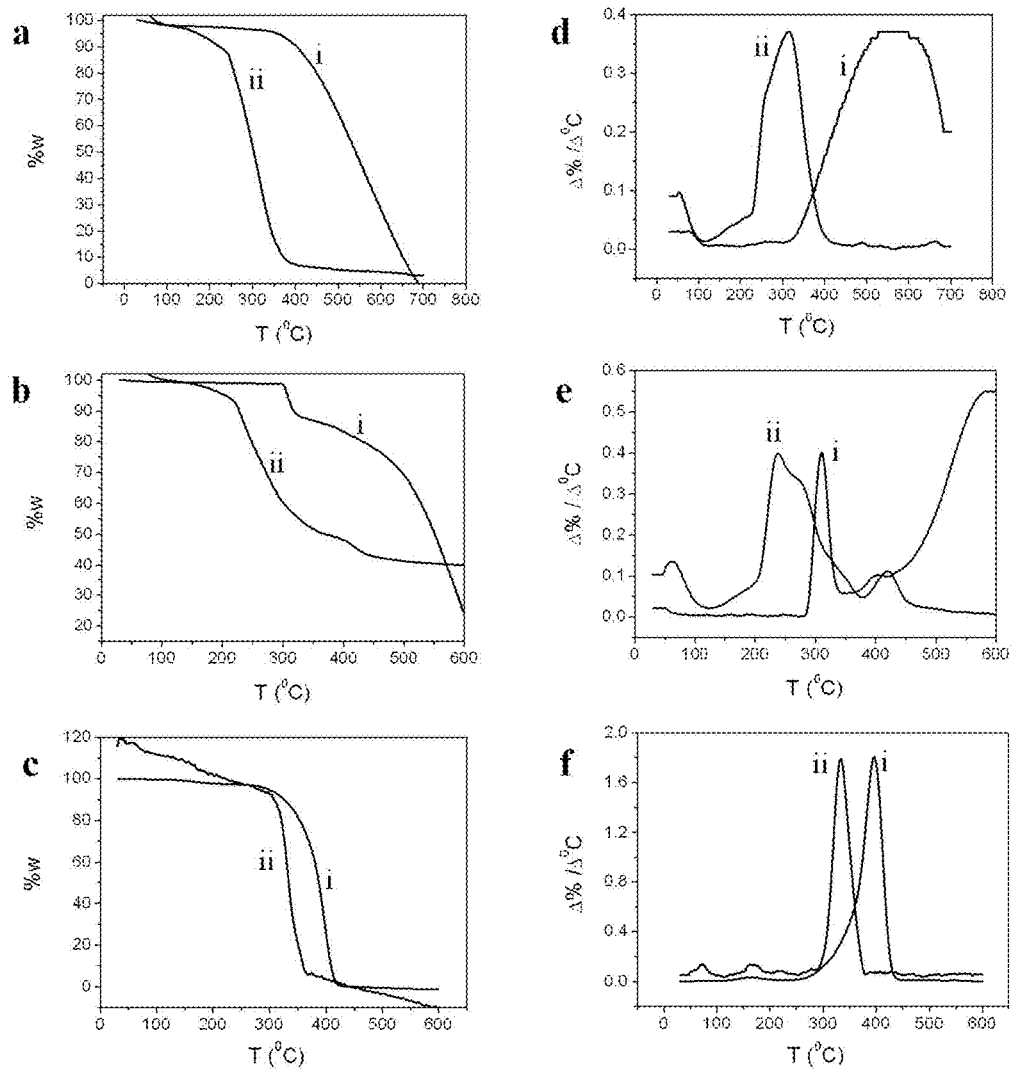
FIGS. 4a-4f shows the thermogravimetric analysis in air of the original polymer (designated i) and the entrapped polymer (designated ii) in: (a) PANI vs. PANI@Ag, and of (b) PAN vs. PAN@Ag. And the first derivative (DTG) of: (c) PANI vs. PANI@Ag, and of (d) PAN vs. PAN@Ag.

Several observations were made with TGA analysis. FIG. 4 presents weight loss traces (which is the weight that the composite lost during heating to high temperature) and their corresponding first derivatives for three composites. As can be seen from FIG. 4a, the loading of the entrapped PANI is 8.5 wt-%, which based on the densities (10.5 and 1.2 g/cm³ for silver and PANI, respectively) amounts to 44 vol-%. In terms of the atomic concentration, the concentration of the organic fraction is 50 atom-%, which—excluding the hydrogen atoms—reduces to 35 atom-%. It is noted that the % weight of organics in the composite including hydrogen atoms (also referred to as "entrapment level") is much higher than in previously reported polymer@metal composites, where it ranged from less than 1 atom-%[4] to 25 atom-%[6]. Also, the efficiency of the entrapment process was quite high, wherein 95% of the original PANI ended up in the composite material. The fact that the occlusion of the polymeric phase in the metallic matrix is mainly by entrapment and not by adsorption is corroborated by the results in Table 4, below. It is seen that compared with the very low adsorption capacity of metallic Ag the overall entrapment is huge.

TABLE 4

Absorption vs. Entrapment

| Sample | Adsorption (%) | Entrapment (%) |
|---|---|---|
| PANI@Ag | 7 | 95 |
| PAN@Ag | 6 | 79 |
| PS@Ag | 1 | 25 |

The second observation made by TGA refers to the catalytic nature of Ag in oxidation reactions, reveled by the first derivative of the TGA trace. The polymer in the composites decomposes at a much lower temperature than the polymer in its free form (FIG. 4d), namely, the decomposition peak of PANI in its free form is ~500° C., whereas that of PANI in the composite is below 300° C. This is accompanied by narrowing the decomposition range to less than 200 centigrade. Both effects reflect the catalytic action of metallic Ag in facilitating the oxidative decomposition of the polymer.

The Entrapment Effect on the Redox Forms of PANT

PANI in its base form consists of two main structural units, i.e., the benzoid diamine and quinoid diamine, shown in Scheme 1, below.

Scheme 1. The structure of polyaniline.

Quinoid diimine          Benzoid diamine

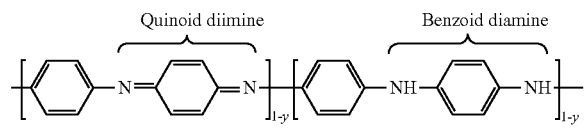

Figures 5A, 5B:
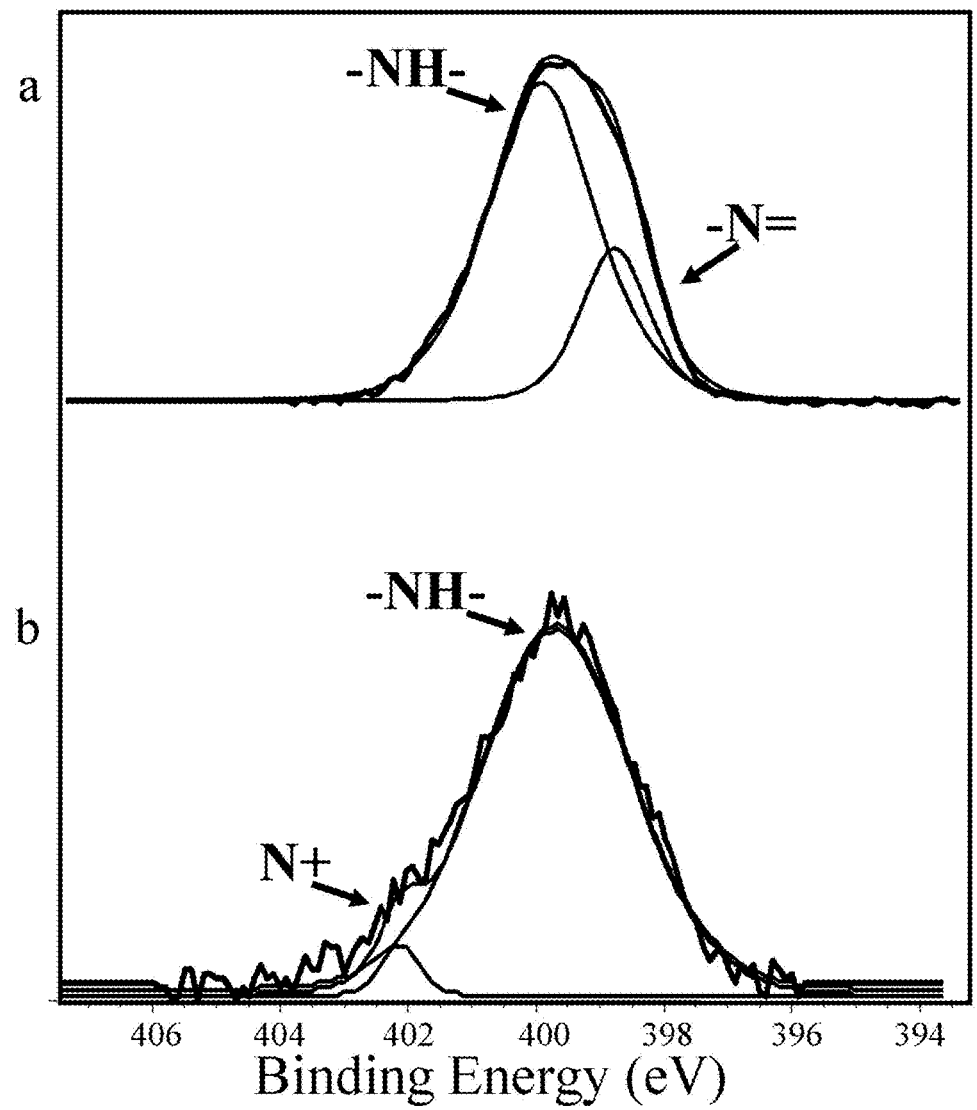
FIG. 5 shows the XPS spectra of N 1s and the deconvoluted peaks for free PANI (a) and for PANI@Ag (b).

The fully oxidized and reduced forms contain only quinoid diamine (pernigraniline) and benzoid diamine (leucoemeraldine) units, respectively. The relative contents of these units—designated redox forms—express intermediate oxidation states, of which the 50:50 randomly distributed composition (emeraldine)—is noted. Based on a number of experimental indications it is theoretically concluded that the main form of the entrapped PANI is leucoemeraldine, implying that the entrapment process entails reduction of the original emeraldine. The first indication comes from the XPS analysis carried out on emeraldine and PANI@Ag. In emeraldine, a broad peak for N 1s is obtained (FIG. 5a), which can be deconvoluted into two N 1s peaks with binding energies of 398.8 and 399.9 eV, assigned to neutral imine [=N—] and amine [—NH—] nitrogen atoms, respectively. This results in a relative proportion of the quinoid and benzoid forms of 23 and 77%, respectively. In PANI@Ag, most of the quinoid form is reduced upon entrapment, as expressed by the dominating [—NH—] peak at 399.8 eV (96.7%) of the deconvoluted spectrum (FIG. 5b). The new peak at 402.2 eV is attributed to an oxidized state of the nitrogen produced during the entrapment process.

Figure 6:
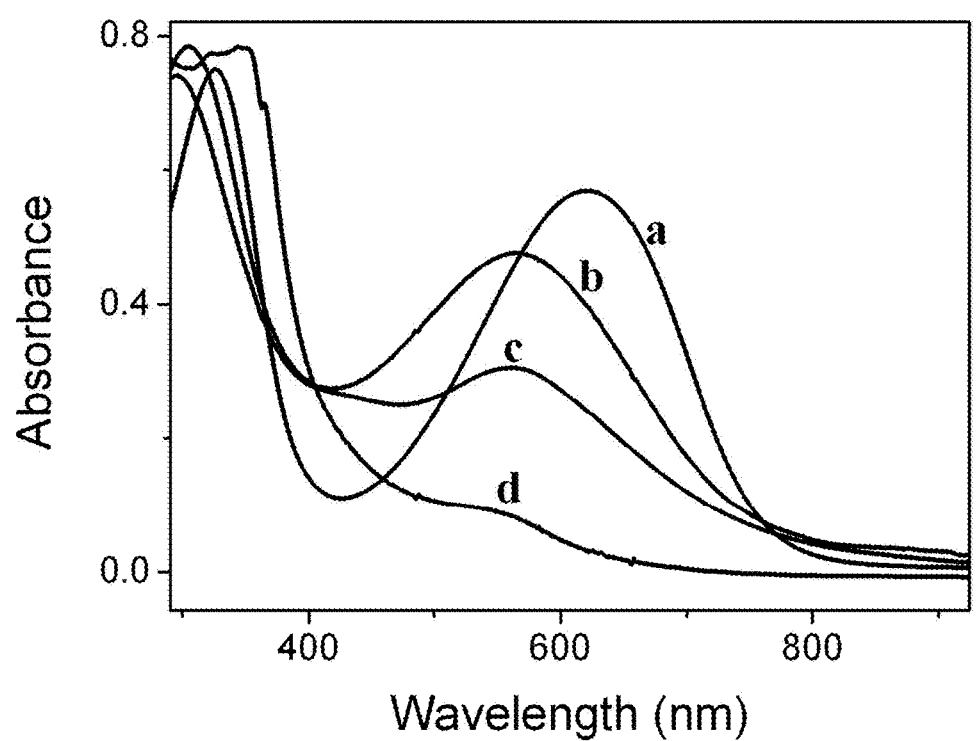
FIG. 6 shows the UV-Vis measurements of PANI in DMSO: (a) Free form of PANI, (b) PANI interacts with macro size Ag particles in the reaction conditions, (c) PANI interacts with nano size Ag particles in the reaction conditions, and (d) the final solution of the entrapment reaction of PANI@Ag.

Confirmation of these observations comes from the analysis of the filtered supernatant solution at the end of the entrapment reaction, which contained 5% of the original PANI. UV-Vis measurements (FIG. 6), considering the ratio of the 320 and 630 nm peaks of the benzoid and quinoid forms, respectively, show that the original ratio of 1.6 in the emeraldine now increases to 8.3, compared with over 15 for the reduced PANI-leucoemeraldine form. Furthermore, the results in FIG. 6 show that the adsorption of PANI onto silver particles did not affect the redox state of the adsorbed polymer, showing that entrapment and adsorption are distinctly different processes.

It is proposed that the reduction of the quinoid diamine units during the entrapment reaction occurs via the electrochemical Ostwald ripening reaction and the formation of the silver nanoparticles. It is noted that the standard electrode potential of a nano size metal particle ($E_p^0$) differs from that of the bulk ($E_{bulk}^0$) and shifts to more negative values as:

$$E_P^0 = E_{bulk}^0 - \frac{2\gamma \upsilon_M}{zFr} \quad (1)$$

where, $\upsilon_M$ is the molar volume, $\gamma$ is the surface tension, z is the lowest valence state, F is Faraday's constant and r is the particle radius. It is seen that $E_p^0$ decreases with r; in fact, the 1/r dependence enhances the effect quite significantly for very small r-values. Thus, nanoparticles are more effective reducing agents than the bulk metal. However, because of the sharp 1/r dependence, most of the PANI reduction reaction will occur at the very early stages by nascent Ag particles. This is confirmed by the UV-Vis spectra in FIG. 6, wherein the results of the entrapment reaction are compared with those of two emeraldine-Ag suspensions. The heights of the 630 nanometer peaks reveal that the effect obtained by decreasing the Ag particle size to the nanometric range is significant, underlining the size effect on the reduction reaction. Apparently, this effect is enhanced further through the entrapment reaction which generates nascent Ag particles.

A Proposed Mechanism for PANI@Ag Formation

Figure 7:
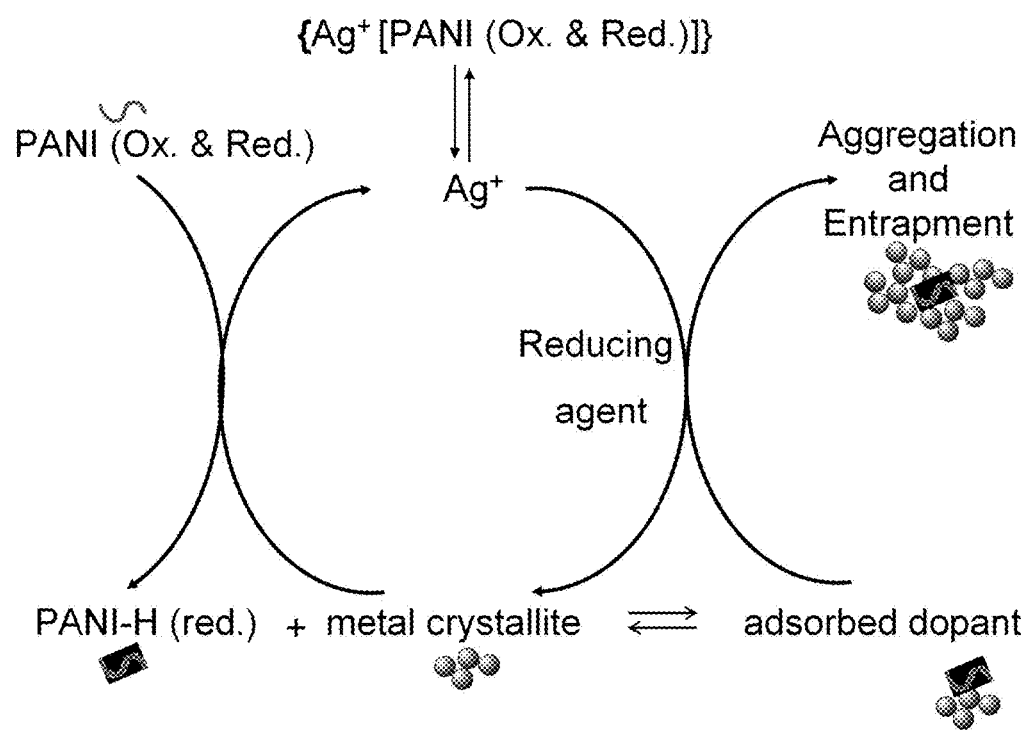
FIG. 7 is as an illustration of a non-binding theoretical proposed mechanism of adsorption vs. entrapment: Top—strong interaction between PANI and silver cations. Left—small metal particles reduce PANI during the entrapment. Bottom—reduction shifts the adsorption equilibrium. Right—adsorbed species entrapped during aggregation.

Based on the observations above, a non-limiting theoretical mechanism for the entrapment of PANI in silver is proposed in FIG. 7.

Scheme 2. The reduction reaction of silver ions by DMF.

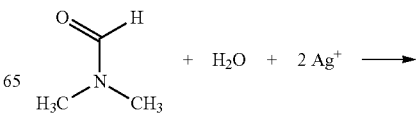

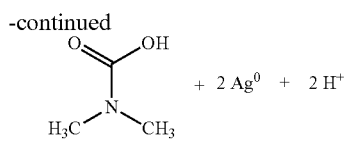

Figures 8A, 8B:
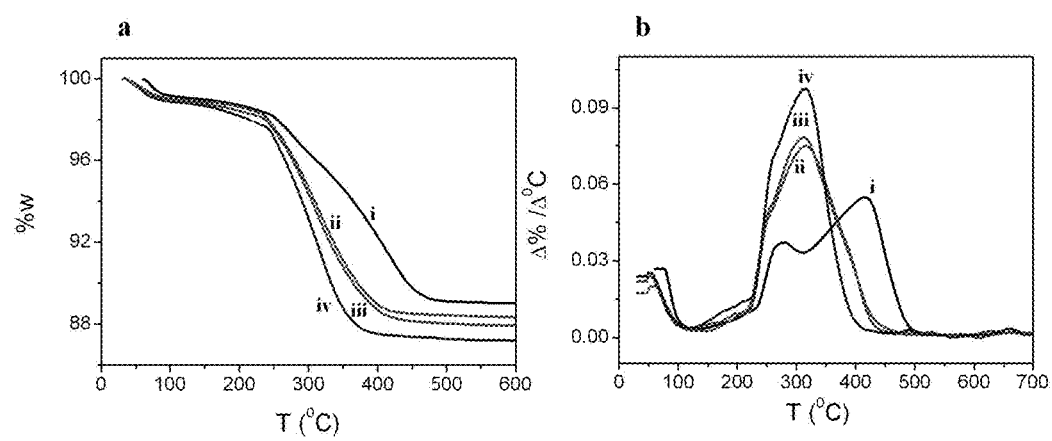
FIGS. 8a-8b shows the TGA of PANI@Ag (a) and its first derivative (b). The influence of the time that silver cations interacts with PANI before the reaction: 0 hours—black (i), 0.5 hours—red (ii), 2 hours—green (iii), 24 hours—blue (iv).

From the reaction equation provided in Scheme 2 it is clear that the reduction reaction is triggered by water addition. Yet, the TGA results (FIG. 8) indicate that the polymer already interacts with the metal cation prior to the onset of the reaction and metal particle formation. This indication is based on the catalytic effect of the silver on the oxidative degradation. It is seen (FIG. 8) that as water addition to the stirred solution of PANI and silver salt is delayed (up to 24 h), the catalytic effect on degradation is increased. Presumably, longer stirring results in an intimate interaction of the polymer with the silver cations, generating more effective $Ag^+$—$N^-$ complexes. This, in turn, leads to tighter interaction of the polymer with the metallic silver, which lowers the temperature at which degradation occurs.

Therefore, the proposed non-limiting mechanism of entrapment (FIG. 7) assumes that a prerequisite for the reaction is a close interaction between the silver cations and the polymer. Then, as the reduction reaction starts, producing nascent silver particles, it is accompanied by reduction of emeraldine to leucoemeraldine. Initially, adsorption interaction between the polymer and the metal occurs, which is gradually converted to entrapment, provided that the residence time of the adsorbed molecule on the metallic surface is smaller then the rate of metal nanocrystal aggregation. In this case, the adsorption equilibrium is disrupted, as the adsorbed species are progressively entrapped within the interstitial porosity and cages of the metal matrix.

Entrapment of Polystyrene and Polyacrylonitrile in Silver

Two additional polymers were selected to demonstrate the generality of the DMF-based entrapment process, namely carboxy terminated polystyrene (PS) and polyacrylonitrile (PAN). Perhaps the most important point associated with changing the polymer was the need to set specific DMF/water ratio and addition sequence for each polymer. Preferably, the entrapment process is carried out in such solvents ratio that a phase separation does not occur.

Additional modifications were also required to allow for specific characteristics of the polymers. For example, the nitrile polymerization reaction (according to Scheme 3, see below) induced by the silver cation demanded a longer mixing period (up to 3 days) before adding water. Also, the insolubility of PS in DMF required a 1:1 toluene:DMF mixture and a small quantity of water (below 1.5%) to prevent phase separation.

Scheme 3. The structure of polyacrylonitrile (a) and the polymerization process which takes place above 180° C. and create a ladder polymer (b).

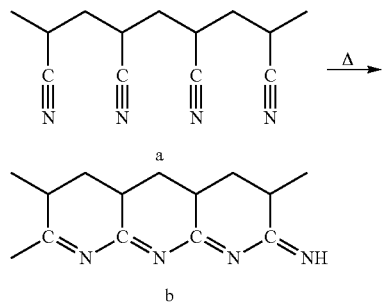

Figures 3A, 3B, 3C, 3D:
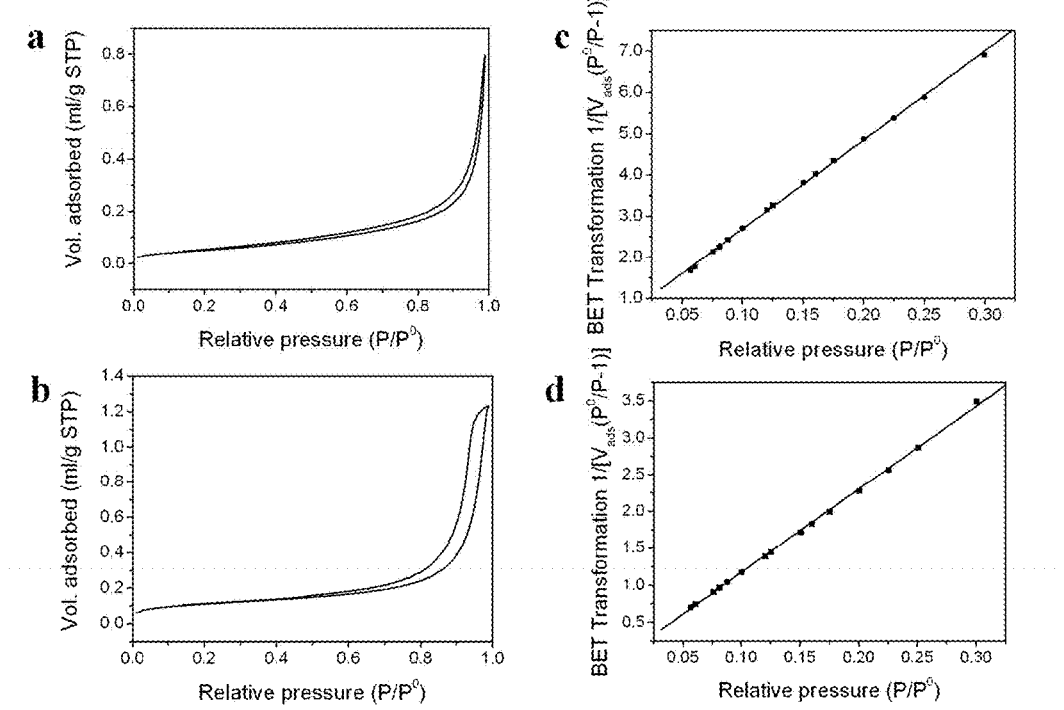
FIGS. 3a-3d shows the adsorption-desorption BET isotherms of $N_2$ for: (a) PANI@Ag and (b) PAN@Ag. And the compliance to the BET equation of: (c) PANI@Ag and (d) PAN@Ag.

A visual textural comparison of the three composites is presented in FIG. 1. Whereas PANI@Ag (FIG. 1b) and PS@Ag (FIG. 1d) are both powdery, PAN@Ag (FIG. 1c) seems rather porous. The higher porosity of PAN@Ag compared with PANI@Ag and PS@Ag is also evident in the SEM photos in FIG. 2 and can be correlated with the respective density values presented in Table 1. It is also seen that the presence of polymer causes reduction in the typical nanocrystal size. The surface area of PAN@Ag is twice that of PANI@Ag (Table 2), in agreement with the density and particle size differences and with the wider BET hysteresis loop of the former (FIGS. 3a and 3b). (The slight increases in the nominal BJH pore size and volume (Table 2) are rational, but may well be within the error range of the measurements and of the inherent error induced by the BJH model).

Several observations can be made on the basis of the TGA results. FIG. 4 indicates that the respective weight percentages of the entrapped PANI and PAN were 8.5% and 6.7% of the composite material and that these high polymer quantities were entrapped quite efficiently: 95 and 79 wt-% of the initial weights of PANI and PAN. Compared with PANI and PAN, the 25 wt-% entrapment yield of PS in PS@Ag is significantly smaller, wherein only 35% of the initial quantity of PS was entrapped in the composite material. This is probably due to the fact that whereas PANI and PAN interact effectively with silver through the nitrogen atoms, the interaction of PS with silver is weak, and—in this particular system—could have occurred mainly through the terminal carboxy groups.

Thus, in some embodiments, the hydrophobic polymers optionally contain one or more electron donating groups, for example, —N, S, $COO^-$, and/or P, and existence of a larger number of these groups on the polymeric chain is expected to favor entrapment.

The lower polymer concentration in the PS@Ag is reflected in the smaller surface area, higher composite density and larger particle size.

The catalytic role of Ag in oxidation reactions is implicit in the TGA results wherein the entrapped polymers decompose at much lower temperatures than the free polymers (FIG. 4). In the case of PAN, nitrile polymerization (Scheme 2b) starts at 300° C. accompanied by oxidation up to and beyond 600° C., whereas in PAN@Ag the Ag-catalyzed cyclization reaction starts at ~200° C. and the degradation ends at ~400° C. (FIG. 4d). In the case of PS the oxidative degradation temperature is decreased by 100° C., from 400 to 300° C. (FIG. 4f).

Figure 9:
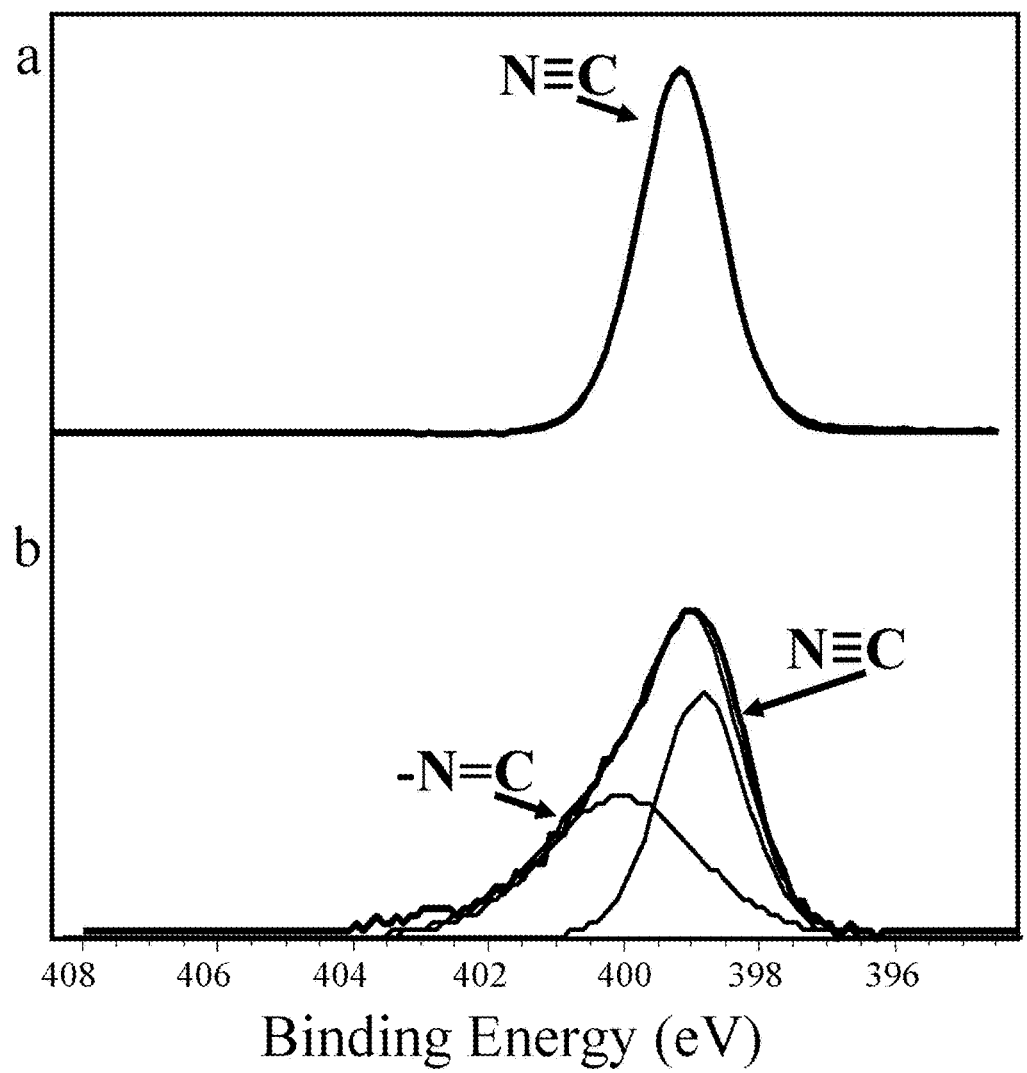
FIG. 9 is XPS spectra of N 1s and the deconvoluted peaks for free PAN (a) and for PAN@Ag (b).
Figure 10:
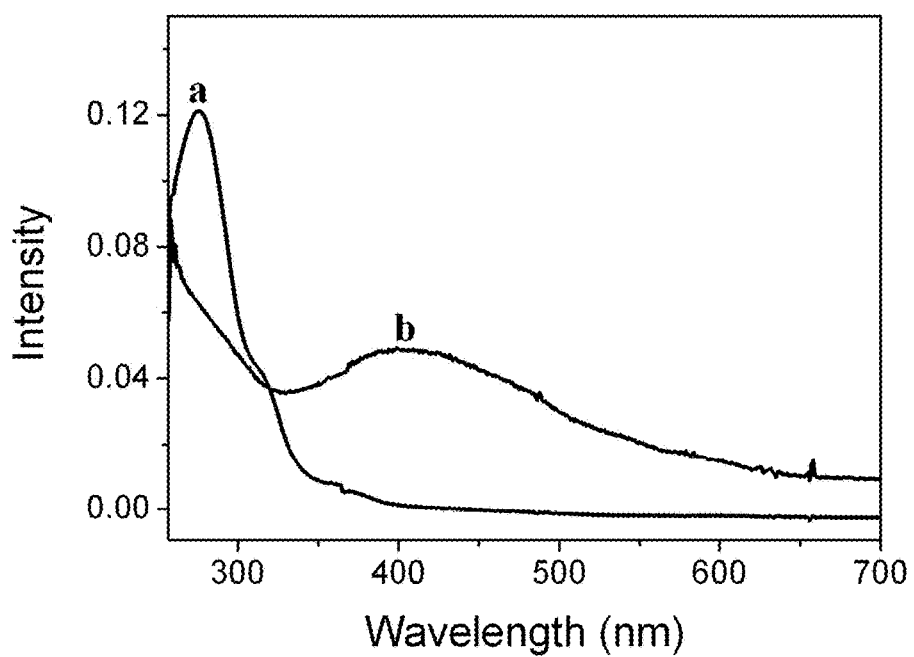
FIG. 10 show UV-Vis measurements of PAN in DMSO (a) and PAN extracted by DMSO from PAN@Ag (b).

The XPS N 1s spectrum of PAN exhibit a single peak at 399.2 eV (FIG. 9a), which is assigned to the cyano group [C≡N]. The same peak in the N 1s spectrum of the PAN@Ag composite decreases to 49.8% of the nitrogens and a new peak at 400.1 eV appears. The new peak is assigned to the imine group [—N═], formed by the Ag-catalyzed nitrile polymerization reaction (Scheme 2). The UV-Vis analysis (FIG. 10) of PAN extracts from the composite (51% of the entrapped polymer) confirms that PAN has undergone partial ladder cyclization, resulting in a typical imine absorption peak around 410 nm, i.e., indicative of the formation of the conjugated-PAN (cPAN) (Scheme 3).

It is assumed that the interaction between the polymer and the metal matrix is different than the preliminary interaction between the polymer and the cation. For the case of PS the metal-polymer interaction are most probably van-der-Vaals interactions, while for the two nitrogen-bearing polymers, the lone-pair of electrons is involved.

Entrappment of Organometallic Complexes

A organometallic complex of rhodium (I) in silver (denoted herein as [Rh]@Ag) was synthesized; and the ability of the entrapped complex to catalyze the hydrogenation of styrene and diphenylacetylene was tested.

The synthesized and tested complex was of the formula (RhCl(COD)(Ph$_2$P(C$_6$H$_4$SO$_3$Na)), where COD stands for 1,5-cyclooctadiene.

The catalyzed hydrogenation reactions demonstrated that a metal can act as a heterogeneous carrier of a homogeneous complex; that the entrapped complex is stabilized by the metallic matrix, in the sense of being protected from reducing agents; and that the nature of the products is affected by the entrapment.

It is also shown that adsorption of [Rh] on Ag and entrapment are different processes, and that entrapment of the hydrogenation catalysts enhances conversion percentage of catalytic hydrogenation.

Materials:

Chemicals: AgNO$_3$, zinc granules (20 mesh (~840 μm)), styrene, chloro(1,5-cyclooctadiene)rhodium(I) dimer and 3-(diphenylphosphino)bezenesulfonic acid sodium salt (TPPMS) were purchased from Aldrich. Diphenylacetylene (99%) was purchased from ACROS.

Preparation of the Rhodium Complex[(Cod)RhCl(L)]=[Rh]

To a methanol solution (10 ml) of the dimeric diene complex of rhodium(I) [Rh(cod)Cl]2 (0.0178 g, 0.036 mmol) was added 0.026 g (0.072 mmol) of Na[(Ph$_2$P-3-(C6H4SO3)] (hereinafter TPPMS, or L) at room temperature. The orange mixture was stirred for 4 hours and then the solvent was removed under vacuum resulting in 43.9 mg, 0.072 mmol (99% yield) of [Rh]. The orange precipitate formed is stable under air.

Entrapment Procedure:

A freshly prepared rhodium complex (43.9 mg, 0.072 mmol) was dissolved in 30 ml of distilled water and then 1.70 g (0.01 mol) of AgNO3 (the molar ratio [Rh]:Ag is 1:139) was added under stirring (750 rpm on a Heidolph MR 3000D stirrer, here and below). After 2 min of stirring, 0.35 g of zinc powder was added and the combined slurry was stirred at room temperature for 6 hours. Silver is formed while entrapping the rhodium complex. Precipitation of [Rh]@Ag begins immediately and is clearly apparent. The precipitate was filtered and washed with 3 portions of 10 ml of water, and dried overnight under vacuum. The final weight of the [Rh]@Ag composite was 1.1 g. 75% (0.054 mmol) of the initial amount of the catalyst was entrapped as determined by UV-vis spectroscopy.

Heterogeneously Catalyzed Hydrogenation Reactions:

The resulting composite [Rh]@Ag (1.1 g) was placed in a 50 ml glass-lined stainless steel autoclave equipped with a magnetic stirrer, containing the appropriate substrate (3.65 mmol of styrene or 2.735 mmol of diphenylacetylene) in 10 ml of 1,2-dichloroethane. After sealing the reaction vessel, it was purged three times with hydrogen, pressurized to 200 psi or 400 psi (for styrene or diphenylacetylene, respectively) and heated with stirring at 800° C. for the required length of time. Upon completion of the reaction, the autoclave was cooled to room temperature, and the composite was separated from the reaction mixture by filtration.

The upper solution was taken for GC analysis. All products are known and were compared with authentic samples. For reuse, the composite was stirred and washed 3 times with portions of 10 ml of 1,2-dichloroethane, and dried under vacuum.

Measuring the Leaching of the Catalyst During the Reaction

For eliminating the possibility of homogeneous reaction due to leaching effect of the complex from the matrix into the solvent, a freshly prepared composite was placed in a glass-lined stainless steel autoclave in 10 ml of 1,2-dichloroethane but without the substrate. After sealing the reaction vessel, it was purged, pressurized and heated as the same conditions of the catalytic hydrogenation reactions. Upon completion of the reaction, the autoclave was cooled to room temperature and unsealed. The composite was separated from the solvent by filtration and the solution was transferred to a new glass-lined stainless steel autoclave which now contained the substrate. The catalytic procedure was performed and the solvent taken for a GC analysis.

Extraction Experiments

Whereas the catalyst could not be extracted with the catalytic reaction solvent—1,2-dichloroethane—extraction could be affected with DMSO. Typically, 1.1 g of the composite was suspended in 30 ml DMSO under constant stirring for 6 h, and the solid was then filtered and washed.

Homogeneously Catalyzed Hydrogenation Reactions with [Rh]

For comparison purpose hydrogenation under homogeneous conditions with the dissolved Rh complex and in the absence of silver was carried out under the same reaction conditions by dissolving it in the reaction solvent mixed with 0.5 ml of methanol needed to achieve full dissolution.

Testing Pure Silver as a Catalyst

For testing the catalytic activity of Ag which is not doped with [Rh], the pure metal was prepared as described above except in the absence of the complex. The resulting metal powder was then used as described above for the heterogeneously catalyzed hydrogenation reactions.

Testing Adsorbed [Rh] on Ag

For comparing entrapment to adsorption, the following experiments were carried out: The pure metal was prepared as described above except for the presence of [Rh].

The resulting metal powder was then stirred for 6 hrs in a water solution of the complex, using the conditions and concentrations of the entrapment procedure. After a similar filtration and drying procedure, the metal powder on which [Rh] was adsorbed (29%, from UV/Vis analysis of the supernatant solution) was taken as the catalyst for the hydrogenation reactions under the same conditions described above.

Testing Adsorbed [Rh] on Ag vs. [Rh]@Ag After Washing With Acid

[Rh]@Ag and [Rh] adsorbed on Ag (prepared as described above) were stirred with 15 ml of HCl (0.1M) for 1 min and then washed 3 times with portions of 10 ml of water. After a drying procedure (vacuum, over night), the resulting materials were tested again as heterogeneous catalysts in the diphenylacetylene hydrogenation reaction, following the same conditions as described above.

Testing the Adsorption of Hydrogen on [Rh]@Ag]

For testing of potential chemisorption, hydrogen was adsorbed on the metal composite at 77K, following the steps described in http://www.micromeritics.com/applications/application_notes.aspx?id=15 (Application note no. 136).

Characterizations and Instrumentation:

Surface area and porosity were determined from adsorption/desorption isotherms of nitrogen on a micromeritics ASAP-2020 instrument, which was also used for testing the adsorption of hydrogen.

SEM was carried out on a Sirion (FEI) HR-SEM instrument (operating voltage is indicated for each picture). UV- Vis absorption spectroscopy was carried out with a Hewlett-Packard 8452A diode-array UV-Vis spectrophotometer. GC separation and analyses were carried out with Agilent Technologies GC model 6820.

Results

The entrapment reaction was carried out according to the following (redox balanced) equation:

[Rh](aq)+2AgNO$_3$(aq)+Zn(s)→[Rh]@(2Ag)(s)+Zn(NO$_3$)$_2$(aq).

The extraction of the entrapped Rh-complex ([Rh]) from [Rh]@Ag indicated that complex remains intact when entrapped. It was found that water, in which [Rh] is soluble and which was therefore used as a solvent for the preparation of the doped metal, could not extract the entrapped complex.

Figure 11:
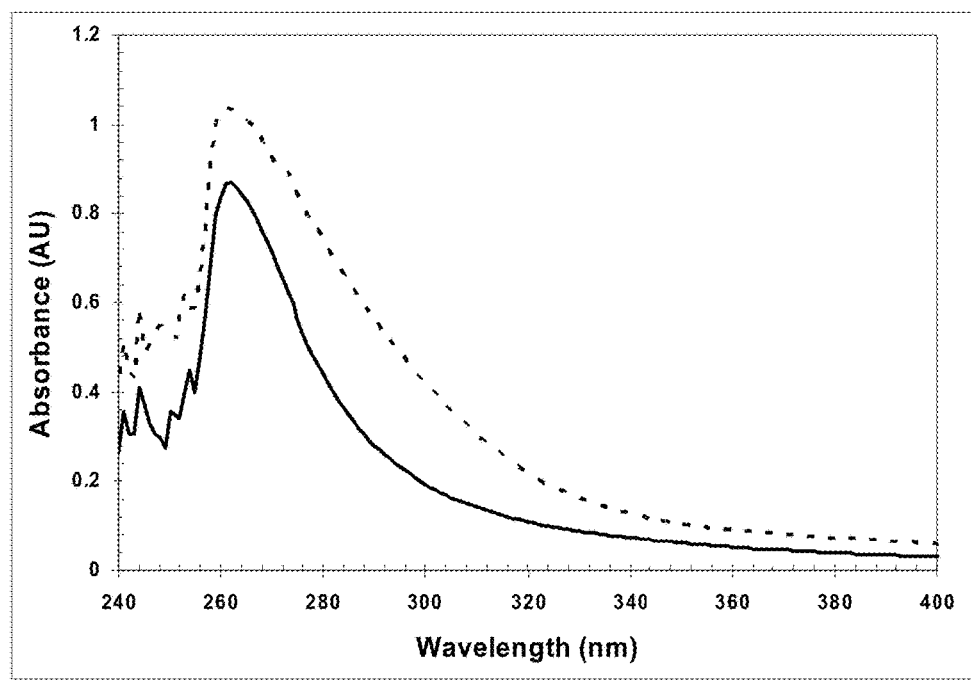
FIG. 11 shows the adsorption spectra of the rhodium(I) catalyst in DMSO before entrapment (dotted line), and after extraction from [Rh]@Ag (smooth line).

DMSO was found to successfully extract the Rh complex from the entrapping silver. As seen in FIG. 11, spectral analysis of the DMSO-extracted catalyst suggests that the complex was kept intact during the entrapment process; although it cannot exclude the possibility that in its entrapped form, the complex is a pre-catalyst to the actually active species.

Nitrogen adsorption-desorption isotherms reveal that the composite is mesoporous with average pore size of 13 nm, and a consequent low surface area of 1.5 m$^2$/g. These values are larger than those obtained for pure Ag synthesized under similar conditions but without the complex: pore size of 5 nm and surface area of 0.3 m$^2$/g. These values suggest that the organometallic complex interferes with the growth process of the silver crystals. Such interference was indeed observed in SEM images, as discussed below.

It should be noted that the surface area value was obtained by using the BET equation, the compliance to which was excellent; such compliance is usually associated with high surface homogeneity of the adsorbing material.

Figures 12A, 12B, 12C, 12D:
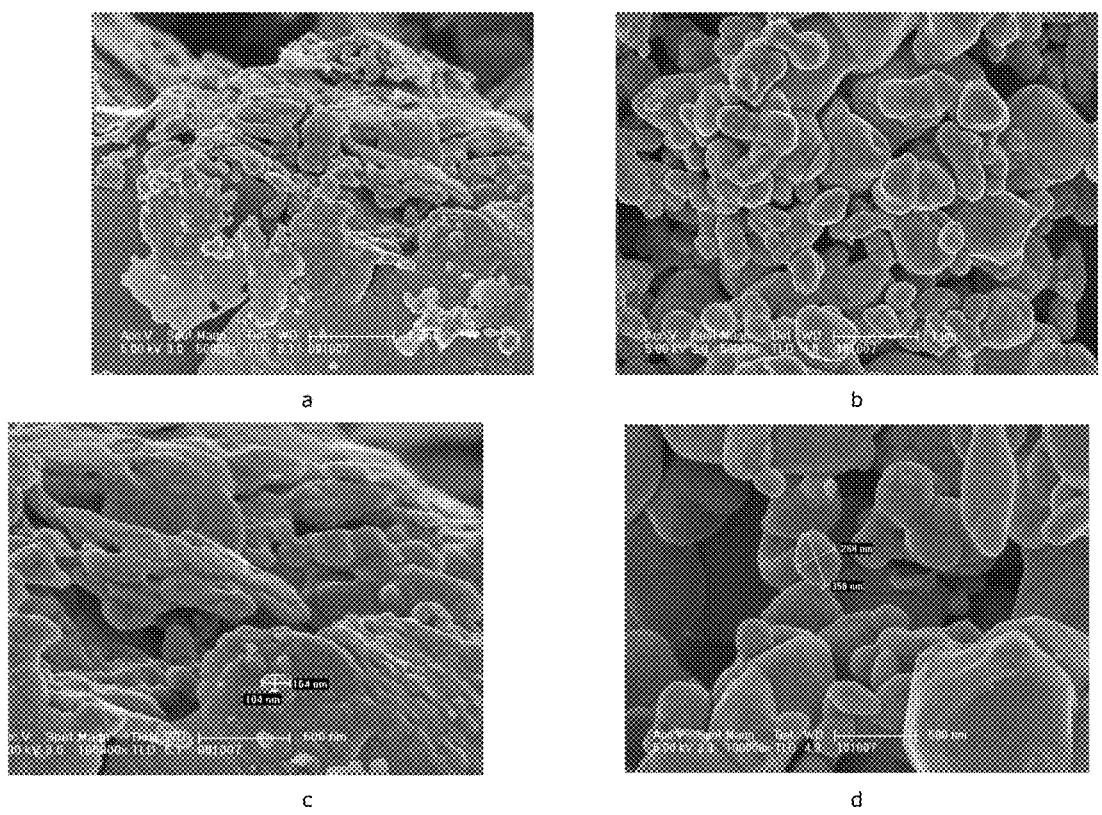
FIGS. 12a-12d shows high resolution SEM images of [Rh]@Ag, ((a): bar=1µ, (c): bar=500 nm), and, for comparison, [Rh] adsorbed on silver ((b): bar=10, (d): bar=500 nm)
Figure 13:
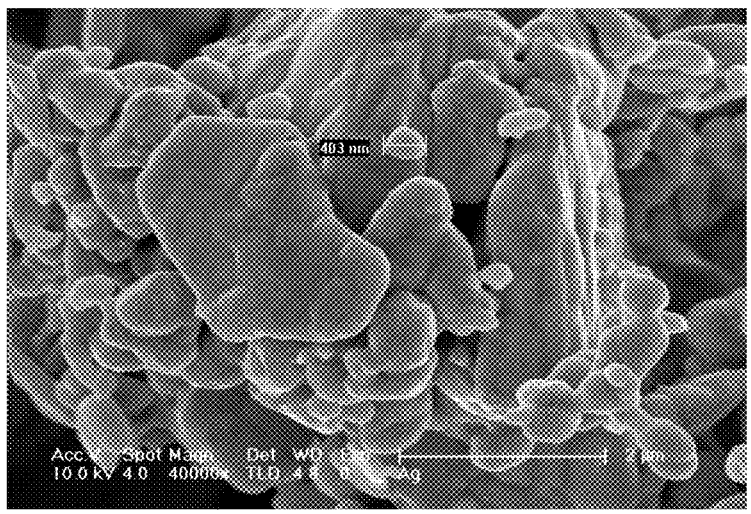
FIGS. 13a-13b show pure silver prepared by the same procedure used for doping (a). Silver on which [Rh] was adsorbed (b). Bars: (a)—2µ); (b)—1µ.
Figure 13:
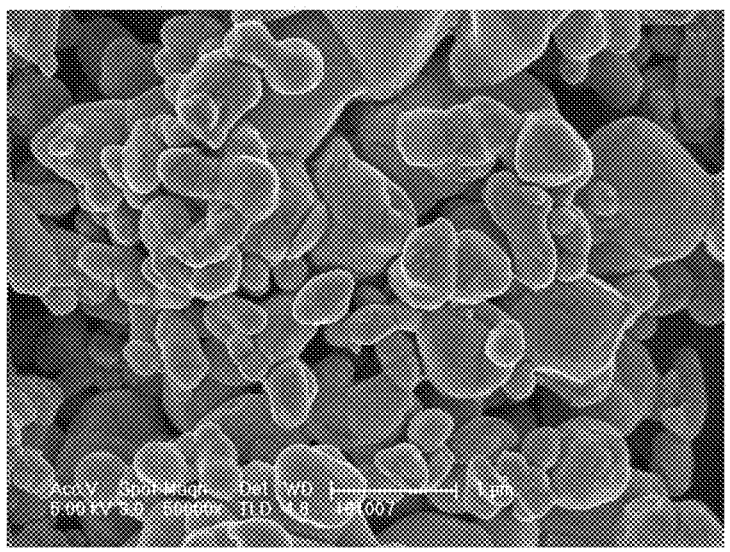

High-resolution SEM further underlines the differences between the doped silver and the pure one: HR-SEM Images of [Rh]@Ag are shown in FIG. 12, and contrasted with [Rh] adsorbed on silver. Smaller crystalline particles, of about 150 nm are seen in the entrapping silver compared to larger crystalline particles, of about 360 nm seen in the SEM of [Rh] adsorbed on silver. This demonstrates one of the differences between entrapment and adsorption. Silver on which [Rh] was adsorbed is affected to a much lesser extent, and resembles the pure silver (FIG. 13).

Another visible distinction between adsorbed and entrapped [Rh] is that [Rh]@Ag is more sheet-like while in the adsorbed case the particles are more spherical.

Figures 14A, 14B:
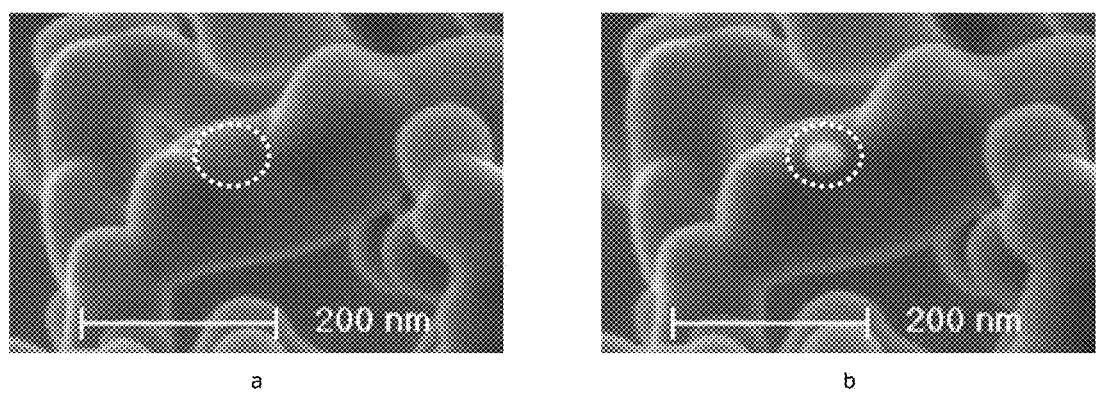
FIGS. 14a-14b show high resolution SEM images for [Rh]@Ag—the oozing out of the organic dopant due to the high energy of the electron beam (see circled area): (a) First taken, and (b) after a few seconds.

Higher resolution is provided in FIG. 14, where it is shown that the entrapped organic complex is observed to ooze out of the composite due to the high energy electron beam focused on the sample. It is assumed that the metal protected the entrapped organic molecule from being destroyed by the focused electron beam, and allowed the organic compound to heat so as to partly get out from the metallic cage.

Figure 15:
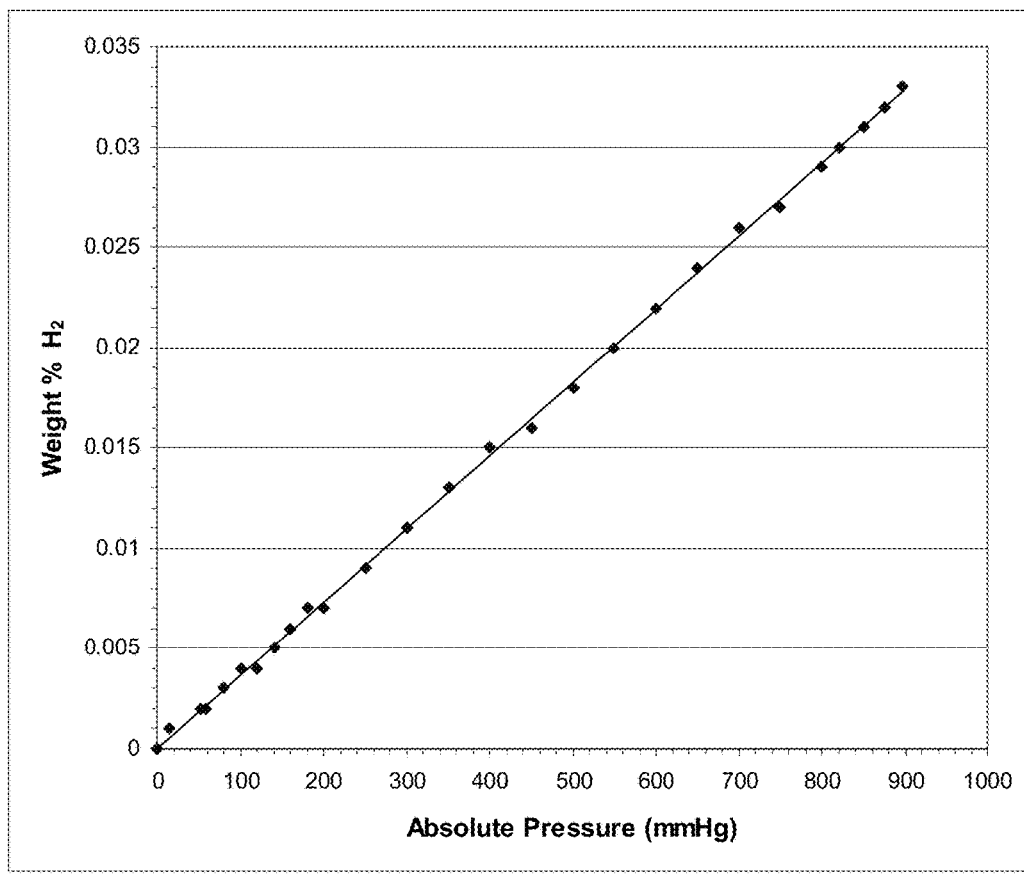
FIG. 15 shows the adsorption of hydrogen on [Rh]@Ag at 77 K.

Adsorption measurements of hydrogen on [Rh]@Ag did not reveal any chemisorption, in agreement with the known fact that hydrogen is not soluble in silver; typically, at 820 mmHg and 77 K, only 0.03 Wt. % of H2 was adsorbed (see FIG. 15). This indicates that the observed effects of the entrapment are not due to synergism between the entrapped complex and the metal, but that the metal is acting here mainly as a protecting matrix which provides confined environment around the [Rh] molecules.

The [Rh]@Ag-catalyzed hydrogenation of styrene (Scheme 4) was carried out in 1,2-dichloroethane under 200 psi of H$_2$ at 80° C. and stopped after 24 hrs at 85% conversion.

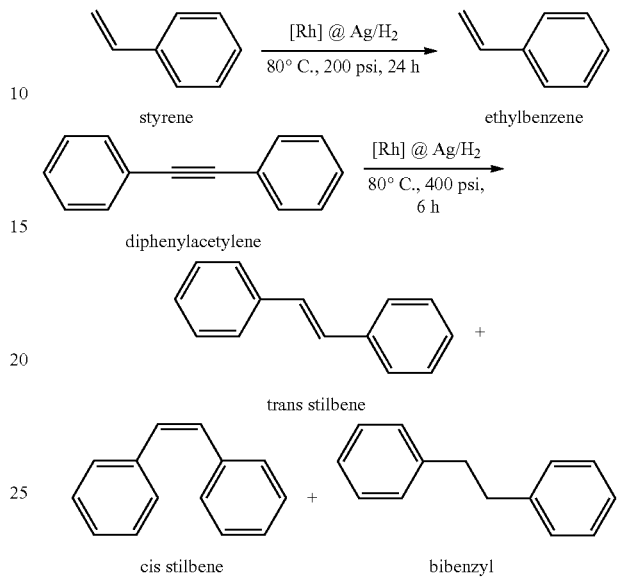

Scheme 4- The catalytic hydrogenation reactions

GC analyses showed that ethylbenzene is the only product of the styrene hydrogenation. Table 5, below, gives the hydrogenation activities of the [Rh]@Ag heterogeneous catalyst, of the dissolved homogeneous rhodium complex catalyst, of the pure Ag metal, and of the rhodium complex catalyst adsorbed on silver. It is seen that the pure Ag is inactive as a catalyst; that adsorbed [Rh] on silver is only marginally active, and that under homogeneous conditions [Rh] affects a 50% conversion, but is destroyed after one cycle. This deterioration is due to reductive formation of metallic rhodium deposit—a black deposit—which is inactive in this reaction. [Rh]@Ag performs better than all of these blanks: The first cycle conversion is the highest (85%) and the easily separated catalyst can be used again, although it loses some of its activity.

TABLE 5

Hydrogenation$^a$ of styrene to ethylbenzene

| Catalyst | Conversion (%) | | |
|---|---|---|---|
| | 1$^{st}$ cycle | 2$^{nd}$ cycle | 3$^{rd}$ cycle |
| [Rh]@Ag | 85 | 65 | 45 |
| Pure [Rh] | 50 | Catalyst destroyed after the first cycle | |
| Adsorbed [Rh] | 7 | 0 | 0 |
| Pure Ag | 0 | 0 | 0 |

$^a$Reaction conditions: 24 h, 80° C., 200 psi
$^b$Conversion determined by GC

UV-Vis and NMR analyses of the liquid phase that was separated from the reaction mixture showed that no detectable [Rh] catalyst had leached into the liquid phase. On the other hand, DMSO extraction of [Rh]@Ag provided an indication that [Rh] remained intact.

The [Rh]@Ag-catalyzed hydrogenation of diphenylacetylene was carried out under a somewhat higher pressure of 400 psi of H$_2$ and was stopped after 6 hrs at 60% conversion. GC and NMR analyses are summarized in Table 6.

TABLE 6

Hydrogenation[a] of diphenylacetylene

| | Conversion (%)[b] | | | | | | | | |
|---|---|---|---|---|---|---|---|---|---|
| | 1st cycle | | | 2nd cycle | | | 3rd cycle | | |
| Catalyst | cis-stilbene | trans-stilbene | bibenzyl | cis-stilbene | trans-stilbene | bibenzyl | cis-stilbene | trans-stilbene | bibenzyl |
| [Rh]@Ag | 44 | 8 | 7 | 32 | 5 | 2 | 20 | 3 | trace |
| Pure [Rh] | 0 | 8 | 32[c] | cannot be recycled | | | — | | |
| Adsorbed [Rh] | 12.5 | 4.5 | trace | cannot be recycled | | | — | | |
| Pure Ag | 0 | 0 | 0 | — | | | — | | |

[a]Reaction conditions: 6 h, 80° C., 400 psi
[b]Conversion determined by GC
[c]After ~3 h: cis - 12, trans - 0, bibenzyl - 20%

These results reveal that cis-stilbene is the main product, while trans-stilbene and bibenzyl are the secondary ones. Preference for the kinetically-dictated cis product was reported before in heterogeneous catalysis, and has been proposed to be due to syn-addition.

Under homogeneous [Rh] catalysis conditions, no cis-stilbene was obtained, and bibenzyl was the main product. At shorter times, cis-stilbene could be detected as an intermediate, e.g., 12% after ~3 hrs.

The homogeneous reaction proceeds to the final reduction product but the conversion is lower, due to the gradual deterioration of [Rh]; [Rh]@Ag, in contrast, can be reused.

Extending the reaction time up to full conversion (90 h), results in cis-stilbene remaining the main product, with an increase in the percentage of bibenzyl (Table 7)

The following experiment provided another proof that entrapment protects the entrapped catalyst much more than adsorption. [Rh]@Ag and [Rh] adsorbed on Ag were treated with an acidic solution of HCl (0.1M) and the resulting materials were tested again as heterogeneous catalysts in the dipenylacetylene hydrogenation reaction.

The conversion in the reaction catalyzed by [Rh]@Ag was still fairly high—50% after 6 hrs—compare to residual 4% in the adsorbed case.

Without being bound to theory, Scheme 5 illustrates a proposed mechanism of the entrapment process.

Scheme 5- Suggested mechanism of heterogeneous entrapment

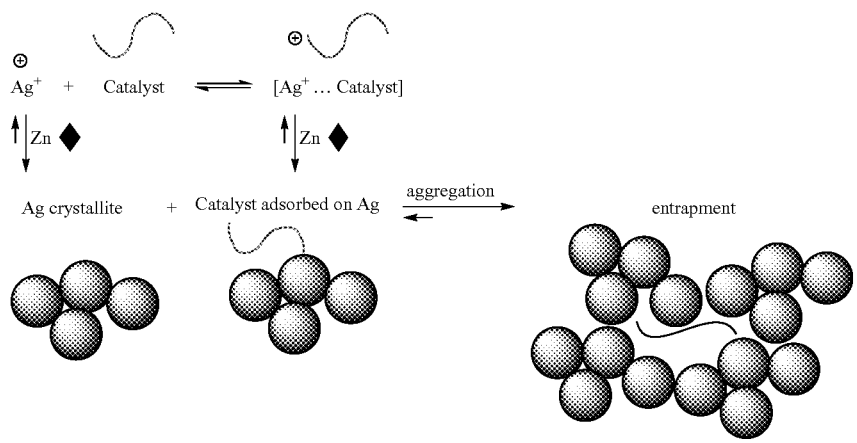

TABLE 7 diphenylacetylene hydrogenation at extended conversions (%)

| Time (h) | diphenyl-acetylene | cis-stilbene | trans-stilbene | bibenzyl | cis/trans ratio |
|---|---|---|---|---|---|
| 6 | 41 | 44 | 8 | 7 | 5.5 |
| 24 | 25 | 57 | 8 | 10 | 7.1 |
| 72 | 8 | 72 | 9 | 11 | 8 |
| 90 | 1 | 74 | 12 | 13 | 6.1 |

In accordance with the mechanism proposed in scheme 5 Silver ion is known to form stable complexes with various atoms of groups V and VI, phosphorous in our case. Thus, it is suggested that shortly after mixing, some ion-pairing occurs between the silver cation and the negatively-charged catalysts, bringing the two into close proximity. As the nanometric seed crystals of Ag form heterogeneously by the Zn particles, the [Rh], already present in the vicinity, associates with these seeds through a reversible adsorption process. The adsorption takes place through the negatively charged sulphonate groups of catalyst and the silver. During the residence time of the adsorbed species, fast precipitation of Ag atoms and clusters catches and encapsulates the molecule. This process thus pumps most of the dissolved [Rh] into a 3D Ag matrix as this matrix is formed.

Indeed, adsorption and entrapment are also different from the point of view of the dimensionality of the event: While adsorption is a 2D process, entrapment results in the Rh complex being surrounded by a 3D metallic cage. This enhances the stability of the entrapped complex in two ways: First, through the physical protection of the rigid cage; and second, through the reductive sea of electrons of the metal, which, apparently, protect the Rh cation from being reduced. Still, the gradual decrease in activity when the entrapped complex is recycled for second and third cycle may point to some in-situ conversion of the Rh cation into metallic Rh.

In conclusion, it was shown that a homogeneous catalyst can be heterogenized by entrapment within a metal. The silver matrix meets the basic requirements of a heterogeneous carrier: Stability to the reaction conditions (temperature and pressure), non-leachability, inertness to the reactants and products, and porosity which is open enough for the transport of the substrates in and out. Since a metal and a dopant can each possess catalystic properties, synergistic effects may be expected.

Some non-limiting examples of organometallic complexes that may be entrapped in metals according to embodiments of the invention are detailed in the tables below:

Rh(CO)$_2$ (acac)
IrCl(CO)(PPh$_3$)$_2$
Pd(OAc)$_2$
RhCl (PPh$_3$)$_3$
Ir$_4$(CO)$_{12}$
PdCl$_2$(PPh)$_2$
RhH(CO) (PPh$_3$)$_3$
[Ir(COD) (PPh$_3$)$_2$]PF$_6$
PdCl$_2$(COD)
[Rh(COD)(PPh$_3$)$_2$]BF$_4$
[Ir(COD)Cl]$_2$
Pd(PPh$_3$)$_4$
[Cp*RhCl$_2$]$_2$; Cp*=C$_5$Me$_5$
[Cp*IrCl$_2$]$_2$; Cp*=C$_5$Me$_5$
PdCl$_2$(CH$_3$CN)$_2$
RuHCl(PPh$_3$)$_3$
Ni(COD)$_2$
Pd$_2$(dba)$_2$
RuCl$_2$(PPh$_3$)$_3$
AuClPPh$_3$
Pt(acac)$_2$
[RuCl$_2$ (h$^6$-p-cymene)]$_2$
NiCl$_2$(PPh$_3$)$_2$
PtCl$_2$(COD)

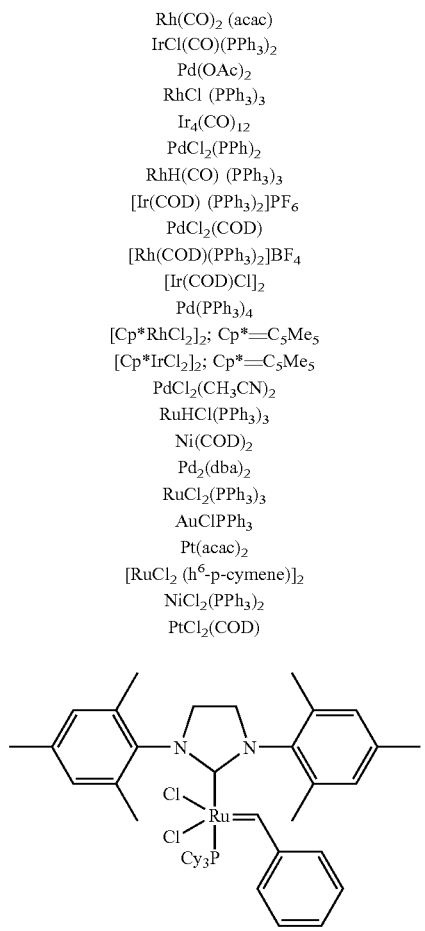

-continued

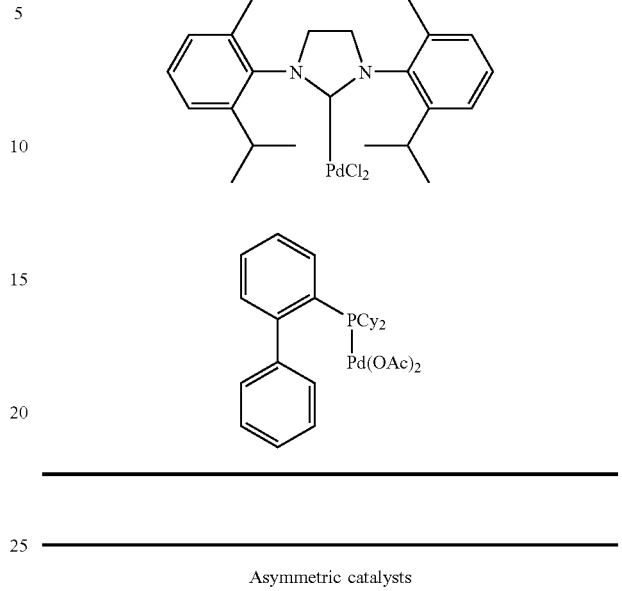

Asymmetric catalysts

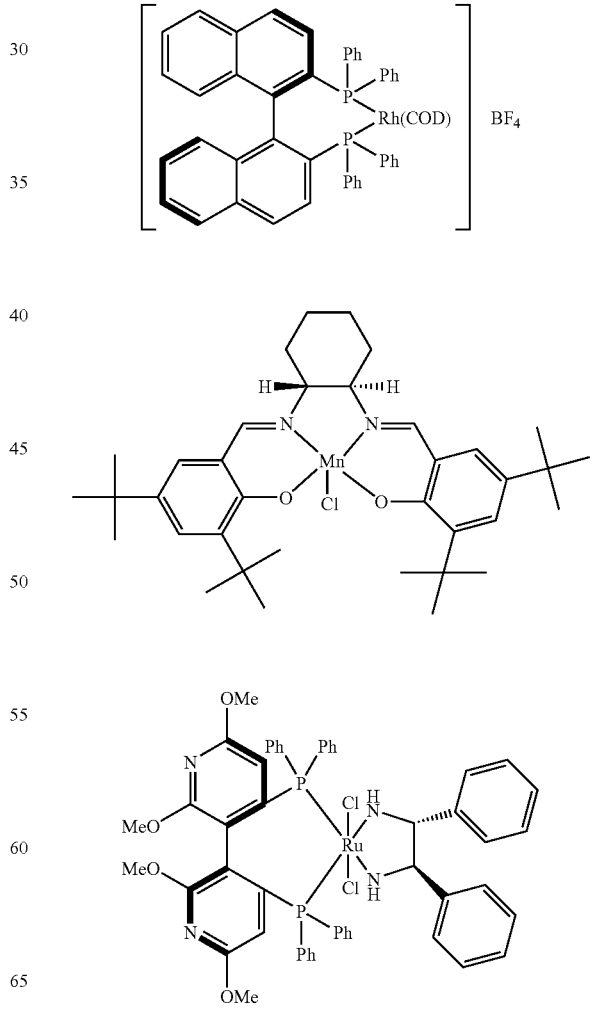

-continued

Asymmetric catalysts

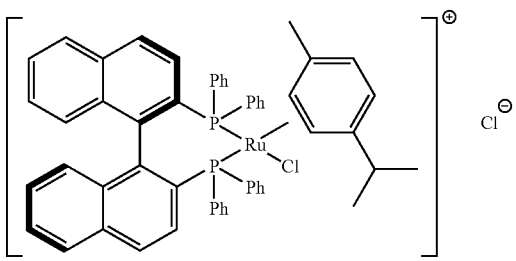

Carbonyl clusters

[NBu$_4$][Ru$_6$C(CO)$_{16}$]   Co$_2$(CO)$_8$   Rh$_4$(CO)$_{12}$   Ru$_3$(CO)$_{12}$

Heteronuclear complexes

Rh$_2$Co$_2$(CO)$_{12}$   [PPN][IrRu$_3$(CO)$_{13}$]   [Et$_4$N][FeCo$_3$(CO)$_{12}$]
RuRh(CO)$_3$Cl(dppm)$_2$   Co$_2$Pt$_2$(CO)$_8$(PPh$_3$)$_2$ Entrapment of Enzymes Acid Phosphatase Acid Phosphatase (AcP) was entrapped by applying heterogeneous entrapment methodology, namely using a sacrificial reducing metal. This methodology was chosen because it is a relatively short procedure and because the reduction does not alter dramatically the pH conditions during the synthesis.

Glycine solutions (pH 4.5) of gold and silver ions were treated with metallic zinc powders in the presence of the enzyme, forming AcP@metal. The enzymatic activity of the resulting dry precipitated powder was measured by exposing it to p-nitrophenyl-phosphate (pNPP) solutions, following spectroscopically the formation of p-nitrophenolate (pNP) according to scheme 6 below.

Scheme 6: Enzymatic conversion of pNPP using a composite of the invention

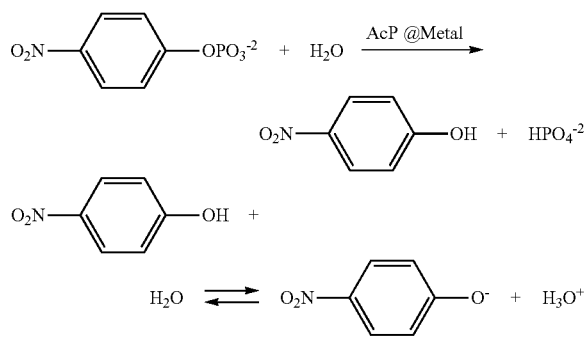

Materials

AgNO$_3$ was purchased from Metalor. HAuCl$_3$.3H$_2$O was purchased from Acros Organic. Zinc granules (20 mesh (~840μ)), acid phosphatase (AcP, cat. no. P-0157), bovine serum albumin (BSA, cat. no. A-7906) and p-nitrophenyl phosphate were purchased from Sigma-Aldrich. Glycine solutions (0.05 M; from Sigma-Aldrich) at pH 4.5 and pH 10.5, containing 1 mM MgCl$_2$ were prepared with the desired volumes of 1.0 M NaOH or 1.0 M HCl.

Entrapment of AcP Within Gold

640 μl AuCl$_3$ solution (0.635 M, 0.406 mmol), 2.85 ml distilled water and 0.6 ml NaOH 1.0 M were stirred to form a solution at pH 4.5. 4.10 ml of glycine-HCl solution (pH 4.5) and 0.04 g (0.609 mmol) zinc powder ((20 mesh (~840μ)) were added and the combined solution was stirred for 15 min. Then, 1.0 ml Acid phosphatase solution (AcP, 0.8 U) was added and the combined slurry was stirred at room temperature (RT) for 24 h. The resulting precipitate was filtered using 0.2 μm cellulose mixed ester membrane, washed with 3×25 ml portions of distilled water, followed by 3×25 ml portions of glycine-HCl solution (pH 4.5) to dissolve and wash out Zn(OH)$_2$ residues, and dried overnight under a vacuum.

Entrapment of AcP Within Silver 0.126 g (0.74 mmol) of AgNO$_3$ was dissolved in 5.0 ml of distilled water. 5.0 ml of glycine-HCl solution (pH 4.5) and 0.024 g (0.367 mmol) of zinc powder were added and the combined solution was stirred for 15 min. Then, 1.0 ml AcP (0.8 U/ml) was added and the combined slurry was stirred at room temperature (RT) for 24 h. Filtrations, washings and drying were carried out similarly as mentioned in the entrapment of AcP procedure above.

Entrapment of BSA Within Silver 1.57 g (9.2 mmol) of AgNO$_3$ was dissolved in 50 ml of distilled water. 0.01 g of bovine serum albumin (BSA) dissolved in 50 ml of distilled water and 0.303 g (4.6 mmol) of zinc powder were added and the combined slurry was stirred at RT for 24 h. The resulting precipitate was filtered and washed with 3×25 ml portions distilled water, 25 ml of HCl 1M and then with 3×25 ml portions distilled water, and dried overnight under a vacuum. The resulting material, 0.8 g of BSA@Ag contained ~100% of the initial polymer used in the reaction mixture, as determined by TGA analysis.

Catalytic Activity Analysis

A sample of 0.02 g of AcP@metal powder was placed in polystyrene cuvettes and were rinsed with 1.0 ml glycine solution pH 4.5, leaving it for incubation at 37° C. for 30 min. Then, the rinsing solution was replaced with 1.0 ml of 10.8 mM of substrate (pNPP) in glycine solution pH 4.5, and the enzymatic activity was measured by following the formation of p-nitrophenolate (pNP) spectroscopically through the absorption at 405 nm, at 37° C. Readings were taken every 5 min for 2 h. The rinsing and the synthesis filtrate solutions were also tested for enzymatic activity by transferring 250 μl of the solutions into cuvettes and placing 1.0 ml of 13.5 mM of substrate (pNPP) solution. The natural hydrolysis of the substrate solution was measured as well, and subtracted from the samples activity. The rates for the enzymatic reaction were calculated and are presented in Table 8. The dose-response kinetics of the composites was measured by using different pNPP concentrations, ranging from 0.27 to 10.8 mM in pH 4.5 glycine solution.

TABLE 8

Rates of catalytic activity

| Adsorption supernatant | Adsorbed AcP (μM/min) | Entrapped AcP (μM/min) | Metal |
|---|---|---|---|
| no activity | 2.81 | 14.9 | Au |
| | 3.56 | 13.4 | Ag |

Protectability Test of AcP@Au

The activity of the entrapped AcP was measured by a similar procedure, bringing the pH of the pNPP solution to pH 10.5 with NaOH and keeping the pNPP concentration at 10.8 mM. For comparison, initial rate of activity of 1.2 μl AcP solution (180 U/ml, 0.2 U) at both pH 4.5 and 10.5 were measured similarly.

Adsorption vs. Entrappment Measurements

For comparing entrapment to adsorption, the following experiments were carried out: Metallic silver and gold powders were prepared as described above but in the absence of AcP. The resulting powders were stirred for 24 h in a pH 4.5 glycine solution of AcP using the conditions and the concentrations of the entrapment procedure. The supernatant solutions and the resulting dry powders were then tested for enzymatic activity as described above.

Surface-Area and TGA Measurements

Typical $N_2$ adsorption-desorption BET surface area of the composites is 0.8 $m^2$/g with pore volume and pore size of 10 μL/g and 50 nm respectively, according to BJH analysis. Thermal gravimetric analysis (TGA) of the BSA@Ag sample was performed from 50 to 800° C. at a heating rate of 10° C./min in flowing dry air, and the weight loss steps were evaluated.

Results

Figures 16A, 16B:
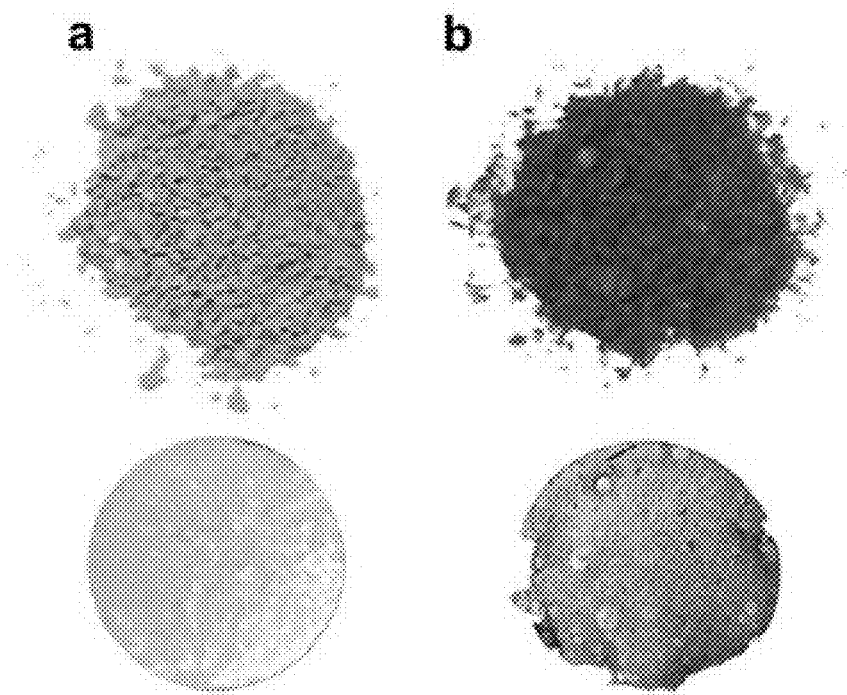
FIGS. 16a-16b shows pictures of enzymatically active metallic composites of the invention, in a powder and pressed coin forms: (a) AcP@Ag (top powder form and bottom coin form) and (b) AcP@Au (top powder form and bottom coin form).
Figure 17:
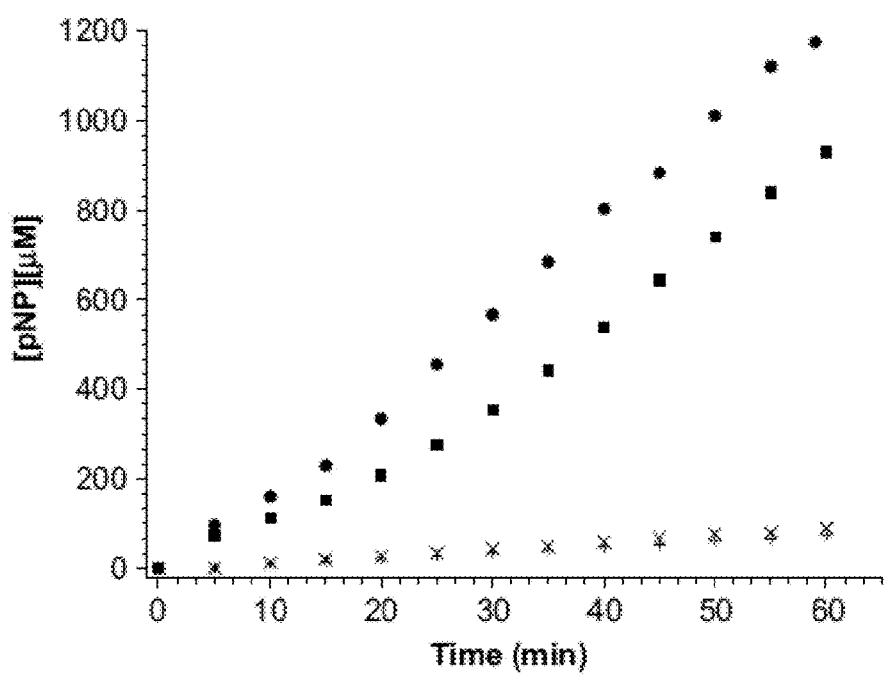
FIG. 17 shows the enzymatic activity of acid phosphatase entrapped within gold and silver: the pNPP hydrolysos activity of AcP@Au (•) and AcP@Ag (■); also shown is the residual hydrolysis activity of the filtrate (+) and of the washing (x) solutions of AcO@Au.

The metallic nature of the composites is clearly seen in FIG. 16 as the composites metallic colors and shine are that of typical silver and gold. FIG. 17 shows that AcP entrapped within gold is active, reaching a rate of 14.9 μM/min after an induction time of 15 min. Two important blank tests are shown as well, namely the testing of possible activities of the washing solutions and of the filtrates: It is seen that the activities of these solutions are negligible (rates of 1.6 and 1.0 μM/min, respectively; this activity is even lower than that of the non-enzymatic hydrolysis at the same pH conditions—2.9 μM/min). It is thus evident that the enzymatic activity of the metallic powder stems solely from the entrapped, non-leachable enzyme. Replacing Au with Ag results in similar enzymatic reactivity (13.4 μM/min, FIG. 17). The similarity between the two metals points to the action of the metals as an inert entrapping matrix. Surface area and porosity analysis indicate that that mesopores are the channels though which the substrate diffuses in, and the product out; the enzyme molecules are entrapped within nano-pores and cages, with pore entrances which allow accessibility to small molecules, but not the leaching out of the protein molecules.

Figures 18A, 18B:
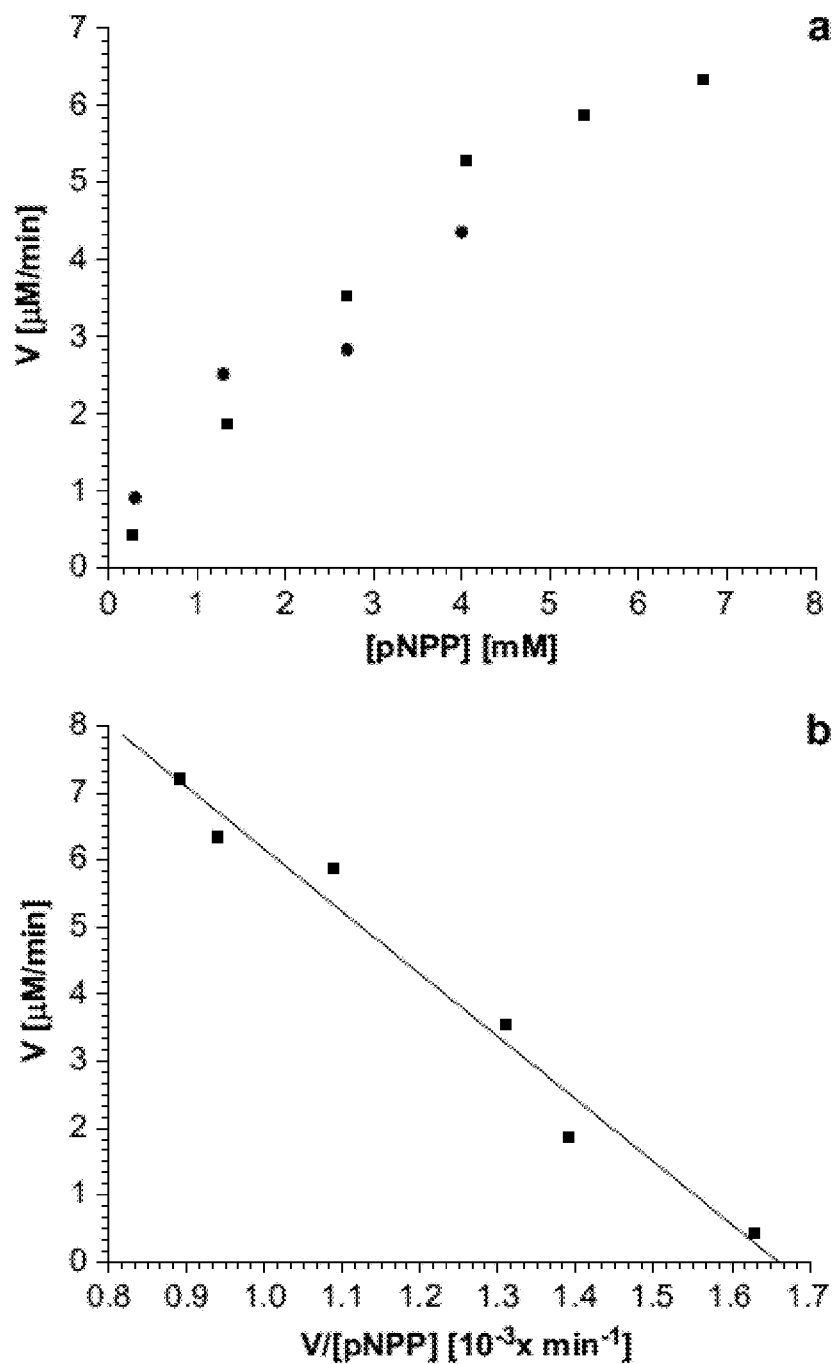
FIGS. 18a-18b show the dose-response curves of AcP@Metal: (a) the enzymatic reaction rates of AcP@Ag (■) and of AcP@Au (•); as a function of pNPP concentration. (b) is an Eadie-Hofstee plot of the AcP@Ag dose-response data.

Kinetics analysis of the enzymatic activity of AcP@Ag at pNPP concentrations below 10.8 mM revealed an apparent Michaelis-Menten behavior (FIG. 18a). Linearization according to the Eadie-Hofstee representation provides a Km of 9.3 mM (FIG. 18b). This apparent Km value is higher than that of the free AcP (1.25 mM), indicating the diffusional restrictions of the substrate and product molecules in and out and within the porous metallic matrix. The dose-response curve of AcP@Au followed a similar trend at low concentrations of pNPP (also shown in FIG. 18a), but was erratic at higher concentrations. As is the case with most other heterogenizing methods in porous media[4], here too, the main cost of entrapment, is the slowing of the reaction rate. However, an interesting gain is the protectability of the metallic matrix: When AcP is placed in a basic solution of pH 10.5 (it is noted that the optimal pH for this enzyme is 4.5), the enzyme is destroyed: Less than 1% of activity was retained. However, when AcP@Au was exposed to these basic conditions, 32% of its hydrolytic activity was retained. Without being bound by theory this protectability ratio can be attributed to the physical cage-confinement limits of the protein's denaturing unfolding-refolding motions. Additionally, it should be noted that the actual value of pH "collapses" within a small cage or pore and loses its bulk thermodynamic interpretation. The confinement within a small cage and the diffusional restrictions render a local nominal value of high basicity, benign.

Figures 19A, 19B, 19C:
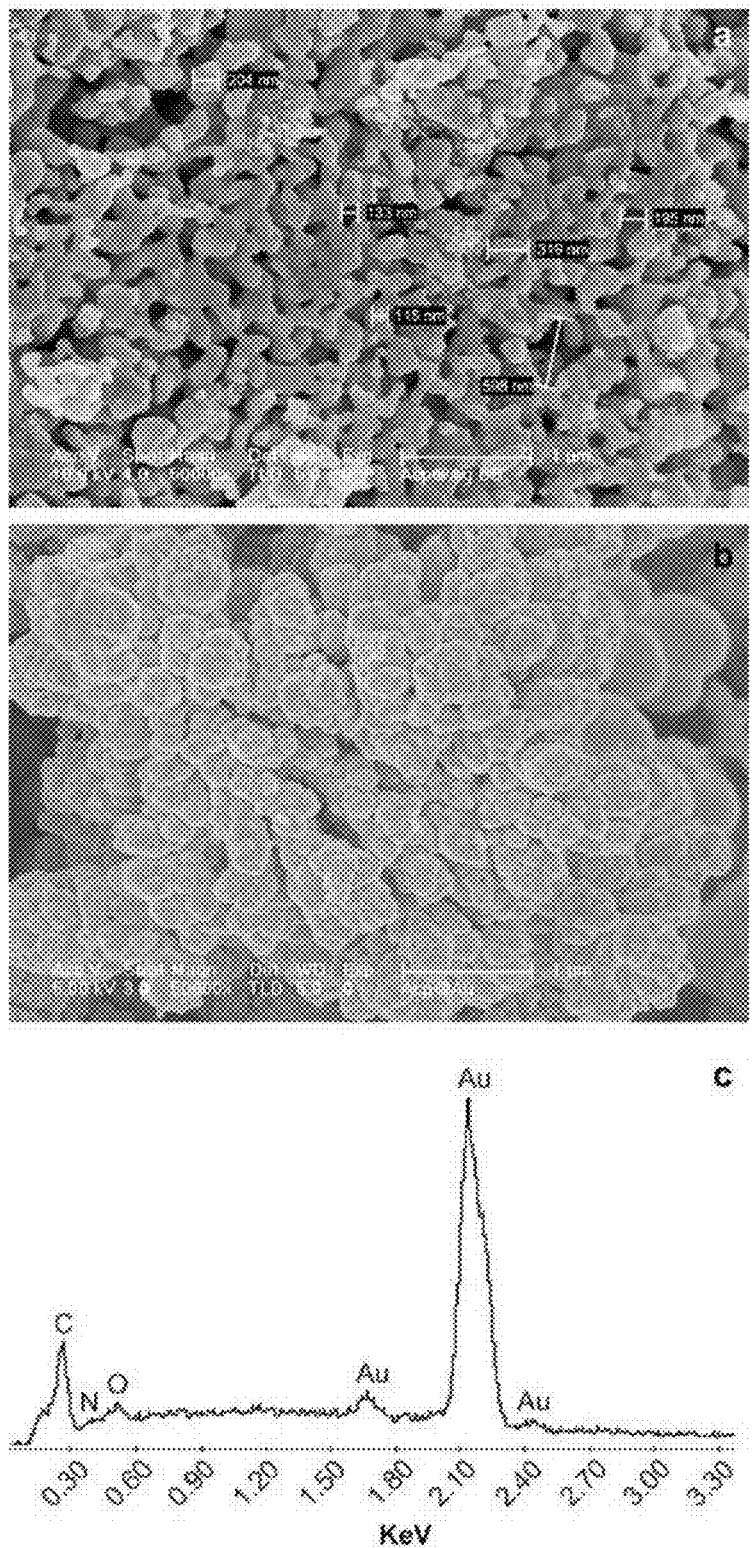
FIGS. 19a-19c is the high resolution SEM images/EDAX analysis of AcP@Metal: high resolution SEM images of (a) AcP@Ag and of (b) AcP@Au (bar=1 µm); and (c) EDAX analysis of (b).

Typical HR-SEM pictures are shown in FIGS. 19a and 19b. It is seen that these bioactive metallic powders are composed of aggregated nanocrystallites. For instance, for AcP@Ag (FIG. 19a), one can see that the morphology varies from ~1μ spherical aggregates to a continuous network of few tens of nm crystallites. The composite nature is manifested by coupling EDAX analysis with SEM imaging: For instance, the large aggregate of AcP@Au seen in FIG. 19b is composed of gold and of the proteins building blocks atoms, carbon, oxygen and nitrogen (FIG. 19c).

Direct determination of the amount entrapped was not possible by standard methods such as TGA because of the minute quantities of enzyme (less than 0.001% w/w), dictated by optimization of the activity. However, in order to get information on protein entrapment yield in general, a model protein of bovine serum albumin (BSA) in a 1000-fold increased loading—1% protein weight/silver weight—was used and the composites oxidative weight loss via thermal gravimetric analysis (TGA) was analyzed; This analysis indicated quantitative (~100%) entrapment of the protein. It is assumed that a similar high-yield entrapment of AcP, which is indeed in agreement with the lack of activity in the washings solutions (FIG. 17).

Figure 20:
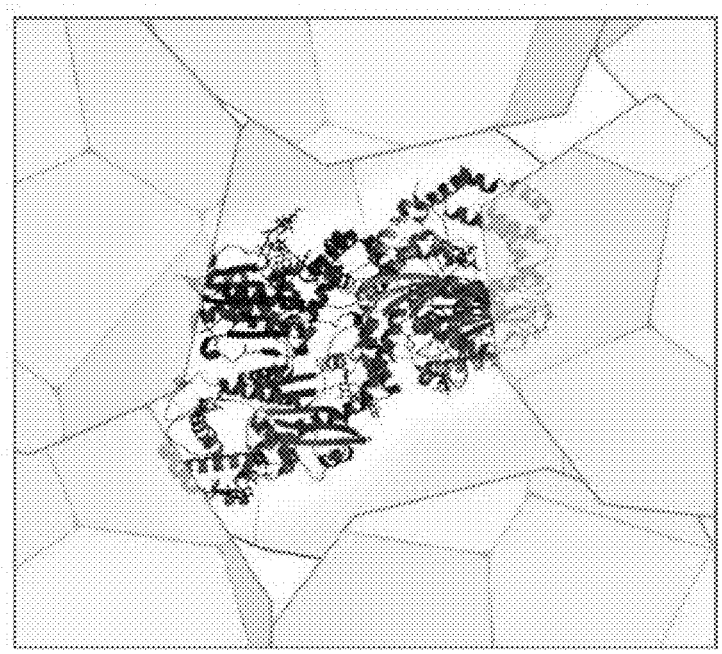
FIG. 20 is a schematic view of the entrapped enzyme within the metal matrix of a composite of the invention.

It is important to note that enzyme entrapment within a metal is a completely different process than the well-known adsorption on metallic surfaces; the former relates to caging of the molecules within the narrow pores of the metallic aggregated matrix (earlier studies indicated that the size range of the elementary building block, the metallic nanocrystallites is typically 15-30 nm). Table 8 compares the two processes from the point of view of the enzymatic activities. It is noted that the reactivities of AcP@Ag and AcP@Au are significantly higher than the corresponding adsorbed configurations. While doping of the metal results in a dispersion which mimics a 3D molecular distribution—the entrapped enzyme is surrounded by metal from all directions (FIG. 20)—adsorption provides a 2D arrangement. This, in turn, allows for better dispersion of the enzyme molecules in the entrapped form. The entrapment picture that arises from our observations is of physical encaging of active enzymes as individual molecules within a porous matrix of aggregated metallic nanocrystallites. The interactions of the entrapped enzymes with the metallic matrix are based on multiple physical and chemical adsorptive interactions through moieties of amino acids on the enzymes surface, such as $-NH_3^+$, $-CO_2^-$ and $-SH$, which are known to have affinity for metallic silver and gold surfaces. These interactions along with the metallic matrix physical barrier can account for the non-leachable nature of the entrapped enzymes.

As these are truly new bioactive materials, only the imagination limits what one can envisage as potential applications. Perhaps the more obvious ones for evaluation are bioactive bone implants, bone scaffolds and bone fracture treatments, medical diagnostics enzymatic electrodes, implants for enzyme deficiency diseases, bioactive endovascular stents, antibacterial gold-coated voice prostheses, and more.

Alkaline Phosphatase

Figure 21:
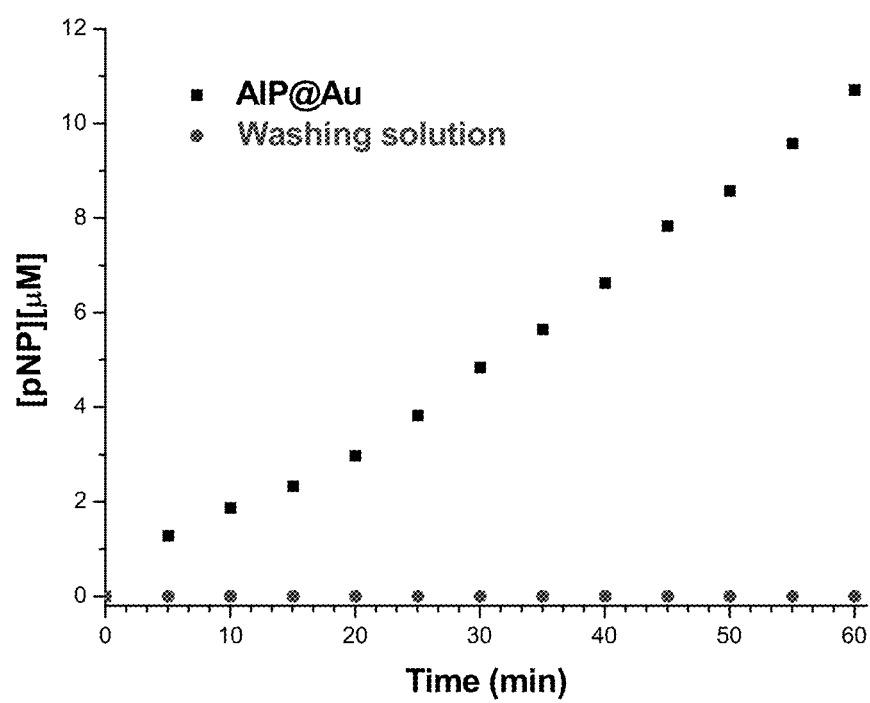
FIG. 21 represents the pNPP hydrolysis of AlP@Au (■) and the residual hydrolysis activity of its washing solution (✱).

Alkaline phosphatase (AlP) which catalyzes the same hydrolysis reaction as Acid phosphatase (AcP) but in basic conditions, was entrapped in a similar method as AcP. FIG. 21 shows the reactivity of the entrapped AlP, reaching a hydrolysis rate of 0.22 µM/min. As in the case of the entrapment of AcP, no activity was measured for the composites' washing solution (also shown in FIG. 21), presenting the non-leachability nature of the entrapped enzyme. However, AlP@Au provided lower reactivity compared to that of AcP@Au, but this difference in activity is in accordance with the difference in activity of the two enzymes in solution—6.5 and 540 µM/min for AlP and AcP, respectively, indicating, again, that the metallic matrix acts mainly as a porous entrapping matrix.

Comparing Adsorption to Entrapment:

Adsorption of AlP on a pre-aggregated metallic gold powder resulted in a similar reactivity rate (0.28 µM/min) to that of the entrapment configuration. The difference between adsorption and entrapment lie in the filtrate solutions: whereas the supernatant of the adsorption experiment showed reactivity of 0.07 µM/min, the filtrate of the AlP@Au composite did not show any reactivity. In the adsorption experiment AlP tends to partition between the metallic powder's external surface and the solution. However, in the entrapment process AlP is trapped within interstitial porosity, and thus no adsorption equilibrium can be established.

Entrapment Procedure:

960 µl $AuCl_3$ solution (0.635 M, 0.610 mmol), 4.10 ml of distilled water and 2.6 ml NaOH 1.0 M were stirred to form a solution of pH 8. Then, 7.6 ml of glycine-NaOH buffer solution (pH 9.5) and 0.06 g of Zinc powder (0.915 mmol) were added and the combined solution was stirred for 15 min. Then, 1.0 ml AlP (1.2 U/ml) was added and the combined slurry was stirred at room temperature (RT) for 24 h. The precipitate was filtered, washed and dried in accordance to the above procedures, except for washing with 6 portions of 25 ml of glycine-HCl solution (pH 4.5; instead of 3 portions) that was followed by one portion of 25 ml glycine-NaOH buffer solution (pH 9.5).

Enzymatic activity analysis and experiments in enzyme adsorption were carried out in a similar fashion as was mentioned for AcP@Au, replacing the glycine solution pH 4.5 with glycine-NaOH buffer solution pH 9.5.

Exemplary Enzymatic Sensor

In an exemplary embodiment, the entrapment of enzymes within metals is utilized in the construction of enzymatic biosensors. The stability of the enzymes in such sensors is enhanced in comparison to the same stability in similar sensors, where the enzymes are not entrapped in metal. The enzyme@metal composite is optionally pressed or sintered to form a plate and used as the biocatalyst component of a biosensor. FIG. 22 is a schematic diagram of a biosensor, which are components of a biosensor utilizing a composite of the invention.

In operation, the biocatalyst, which contains enzyme@metal plate, (a) converts the substrate (S) to product (P). This reaction is determined by the transducer (b) which outputs an electrical signal. The output from the transducer is amplified in amplifier (c), processed in processor (d) and the processing results are displayed on display (e).

The transducer component makes use of a chemical and/or physical change involved in the enzymatic reaction. In various embodiments, this change includes one or more of: (1) heat change (released or absorbed) by the reaction (calorimetric biosensor), (2) changes in the distribution of charges causing an electrical potential to be produced (potentiometric biosensor), (3) movement of electrons produced in a redox reaction (amperometric biosensor), (4) light emittance during the reaction or a light absorbance difference between the reactants and products (optical biosensor) and/or (5) effects due to the mass of the reactants or products (piezo-electric biosensor).

The invention claimed is:

1. A powder composite, comprising:
   at least one molecule of at least one hydrophobic organic compound; and
   a matrix of at least one metal,
   wherein said at least one molecule of said at least one hydrophobic compound is entrapped within said matrix so that said at least one molecule of said at least one hydrophobic compound forms a hybrid with said at least one metal and is surrounded and immobilized by metallic particles and retained within said at least one metal matrix; and
   wherein said composite is in the form of a powder.

2. The powder composite of claim 1, wherein said at least one molecule of at least one hydrophobic organic compound is selected from at least one hydrophobic oligomer, at least one hydrophobic polymer, at least one hydrophobic enzyme, at least one hydrophobic organometallic complex, or any mixtures thereof.

3. The powder composite of claim 1, wherein said entrapped at least one molecule of at least one hydrophobic compound is retained within said matrix.

4. The powder composite of claim 2, wherein said at least one molecule of at least one hydrophobic oligomer or polymer have a molecular weight of at least 10 kdalton.

5. A composite according to claim 2, wherein said at least one hydrophobic enzyme is selected from a hydrolase enzyme, an esterase enzyme and a peptidase enzyme and any mixture thereof.

6. A composite according to claim 2, wherein said at least one hydrophobic organometallic complex is a transition family element organic complex.

7. The powder composite according to claim 1, wherein said at least one metal is selected from Au, Ag, Cu, Zn, Pt, Pd, Ti and Co, and any mixtures thereof.

8. The powder composite of claim 1, wherein the ratio between entrapped at least one molecule of at least one hydrophobic compound and at least one metal is from about 0.05 to about 20 weight %.

9. The powder composite according to claim 1, wherein said metal matrix has pore size of between about 0.1 to about 30 nm.

10. The powder composite according to claim 1, having a surface area of between 0.1 and 20 $m^2$ per gram, as determined by $N_2$-BET.

11. A composition comprising at least one powder composite according to claim 1.

* * * * *